United States Patent
Senderowicz et al.

(10) Patent No.: US 10,918,646 B1
(45) Date of Patent: Feb. 16, 2021

(54) METHODS OF TREATING MYELOPROLIFERATIVE DISORDERS

(71) Applicant: Constellation Pharmaceuticals, Inc., Cambridge, MA (US)

(72) Inventors: Adrian Senderowicz, Somerville, MA (US); Michael Cooper, Cambridge, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/065,316

(22) Filed: Oct. 7, 2020

Related U.S. Application Data

(63) Continuation of application No. PCT/US2019/063515, filed on Nov. 27, 2019.

(30) Foreign Application Priority Data

Nov. 27, 2018 (WO) ................. PCT/US2018/062534
Nov. 5, 2019 (WO) ................. PCT/US2019/059784

(51) Int. Cl.
  *A61K 31/55* (2006.01)
  *A61P 35/00* (2006.01)

(52) U.S. Cl.
  CPC .............. *A61K 31/55* (2013.01); *A61P 35/00* (2018.01)

(58) Field of Classification Search
  CPC ...................................................... A61P 35/00
  See application file for complete search history.

(56) References Cited

U.S. PATENT DOCUMENTS 8,796,261 B2 * 8/2014 Albrecht ................. A61P 31/04
                                                                    514/215

OTHER PUBLICATIONS

Albrecht et al. Identification of a Benzoisoxazoloazepine Inhibitor (CPI-0610) of the Bromodomain and Extra-Terminal (BET) Family as a Candidate for Human Clinical Trials. J Med Chem. 59(4): 1330-9. (2016).
Anonymous: CPI-0610 receives fast track designation for MF. MDedge Hematology and Oncology. 2018 (3 pages). Retrieved on Jul. 22, 2019 from URL: <https://www.mdedge.com/hematology-oncology/article/184600/cythemias/cpi-0610-receives-fast-track-designation-mf>.
Form S1 Registration Statement for Constellation Pharmaceuticals Jun. 22, 2018 (945 pages).
Kremyanskaya, et al. A Phase 2 Study of Cpi-0610, a Bromodomain and Extraterminal (BET) Inhibitor, in Patients with Myelofibrosis (MF). Blood: 132 (Supplement 1): 5481. (2018). (Abstract Only, 5 pages). Retrieved on Jul. 22, 2019 from URL: <http://www.bloodjournal.org/content/132/Suppl_1/5481>.
NCT02158858 Clincal.trials.gov, dated Feb. 20, 2018 (3 pages).
NCT02158858 Clincal.trials.gov, dated Nov. 22, 2016 (4 pages).

* cited by examiner

*Primary Examiner* — Erich A Leeser
(74) *Attorney, Agent, or Firm* — McCarter & English, LLP; Steven G. Davis; Michael J. DeGrazia

(57) ABSTRACT

The present disclosure relates to the use of 2-((4S)-6-(4-chlorophenyl)-1-methyl-4H-benzo[c]isoxazolo[4,5-e]azepin-4-yl)acetamide, and pharmaceutically acceptable salts thereof, for treating myelofibrosis.

30 Claims, 28 Drawing Sheets

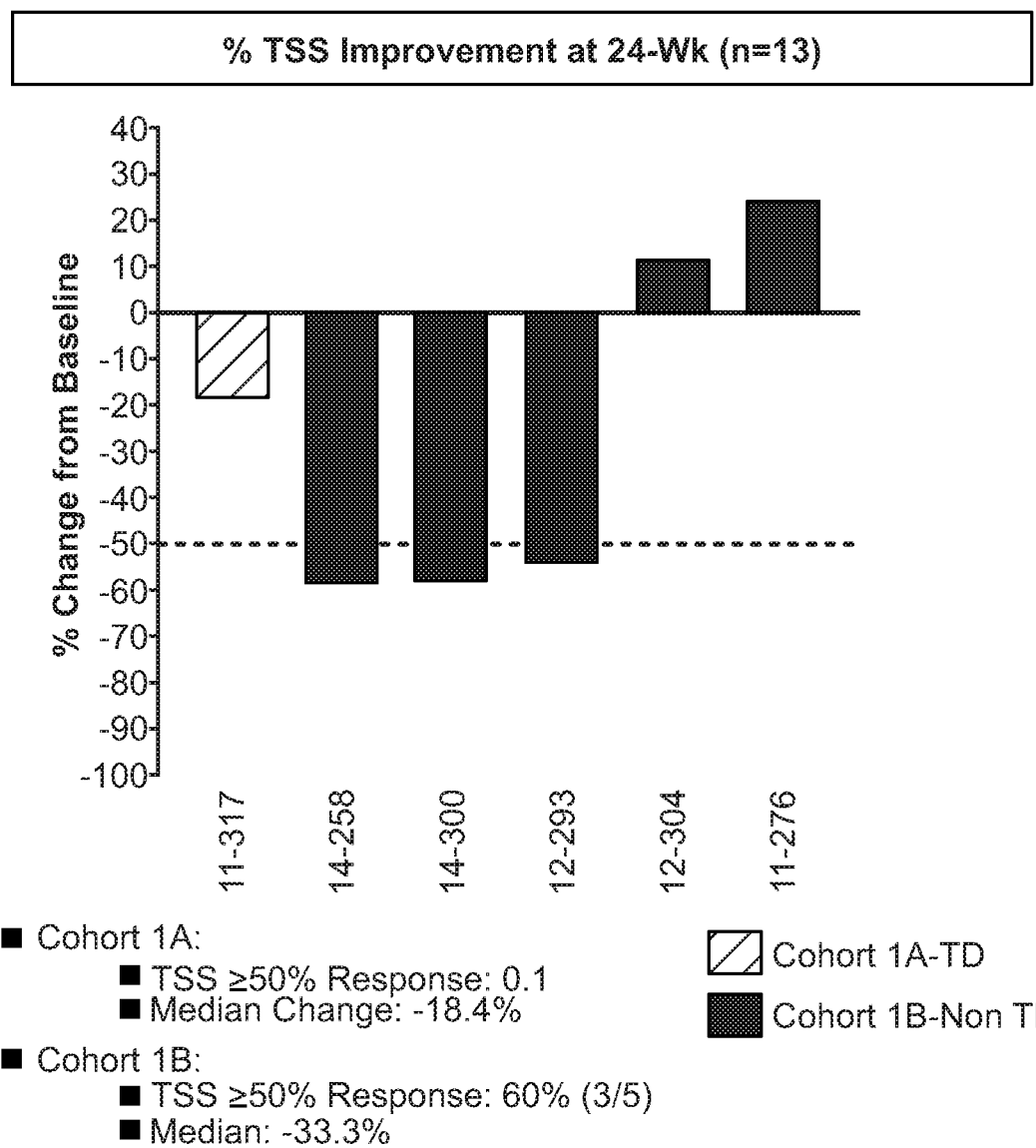

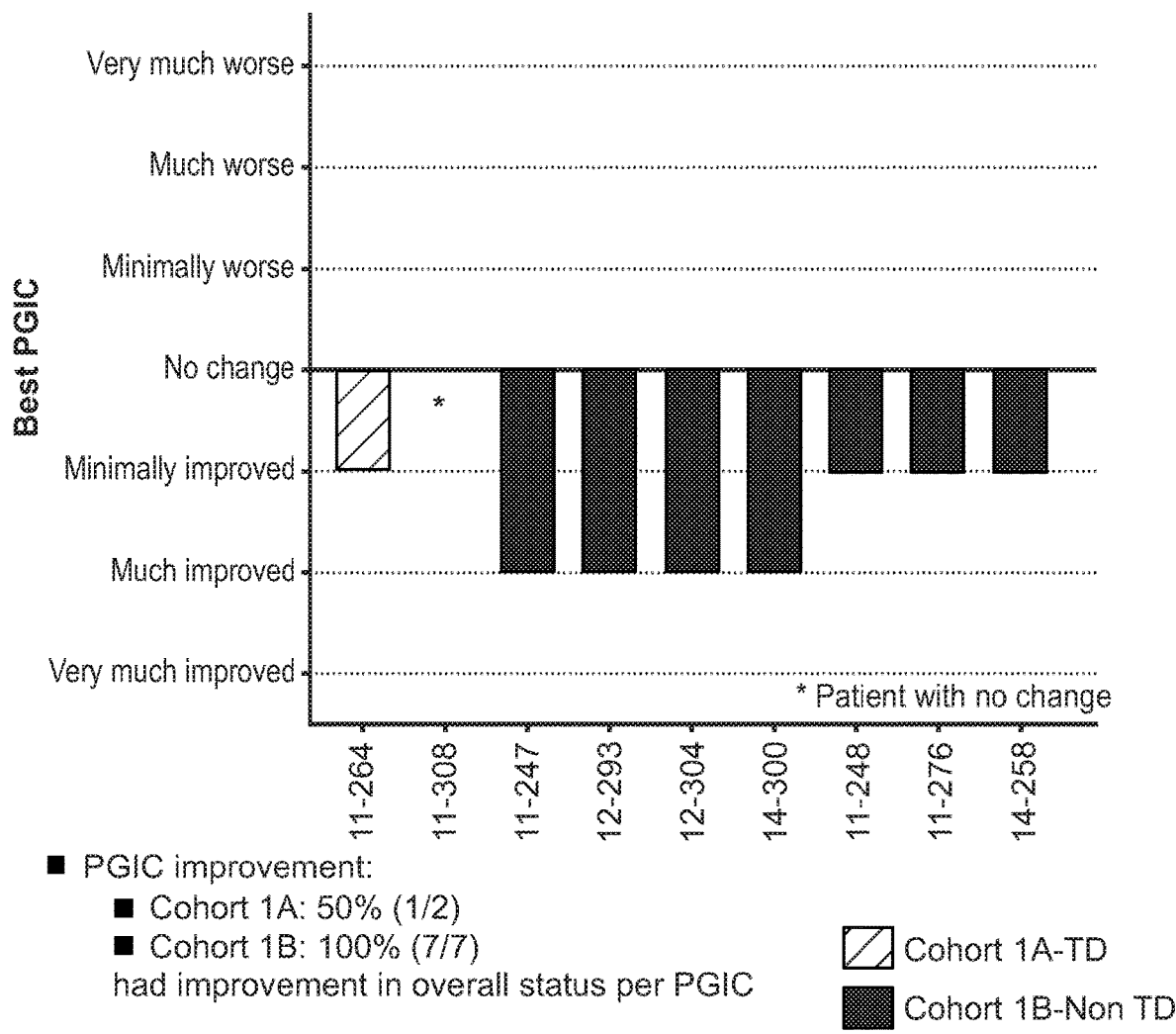

FIG. 14

| Treatment Arm | Cohort | Bone Marrow Fibrosis Grade* | | | | SVR | PRO | ≥1.5 Hgb ↑ | TD →TI | HMR mutations |
|---|---|---|---|---|---|---|---|---|---|---|
| | | Baseline | 24 Wk | 36 Wk | 72 Wk | Best % | Best % TSS or PGIC | Y/N | Y/N | Y/N |
| Cohort 1B (n=8) | Non-TD | 3 | 3 | 2 | 1 | -25.4 | PGIC→ | Y | NA | Y |
| | | 2 | 1 | 1 | 1 | -10.9 | PGIC→ | Y | NA | Y |
| | | | | | | | | | | |
| Cohort 2A (n=11) | TD | 3 | 2 | 2 | 2 | -50.7 | PGIC→ | Y | Y | N |
| | | 2 | 2 | 2 | | -29.5 | -45.5 | Y | Y | Y |
| | | 2 | 1 | | | -8.6 | -8.6 | N | Y | N |
| | | 3 | 0 | | | -19.4 | -100.0 | N | N | Y |
| | | 3 | 2 | | | -8.4 | -47.2 | N | N | Y |
| | | 3 | 2 | | | -40.1 | -83.1 | Y | Y | N |
| | | 3 | 2 | | | -47.0 | -17.6 | N | N | Y |
| | | | | | | | | | | |
| Cohort 2B (n=12) | Non-TD | 3 | 2 | | | -21.9 | -44.8 | N | NA | Y |
| | | 3 | 1 | 3 | | -17.0 | -87.4 | N | NA | N |
| | | 3 | 2 | | | -20.8 | 89.4 | Y | NA | Y |

1 HMR = High Molecular Risk (patients with one of these mutations: *ASXL1*, *EZH2*, *IDH1/2*, *SRSF2 and U2AF1*)
2 Bone marrow evaluable population: Baseline Bx available and at least 1 marrow @ or after 24 weeks \* Per the European consensus on grading bone marrow fibrosis and assessment of cellularity
(Thiele J et al. Haematologica. 2005;90:1128)

METHODS OF TREATING MYELOPROLIFERATIVE DISORDERS

RELATED APPLICATIONS

This application is a continuation of International Application No. PCT/US2019/063515, filed Nov. 27, 2019, which claims priority to International Application No. PCT/US2018/062534, filed Nov. 27, 2018 and International Application No. PCT/US2019/059784, filed Nov. 5, 2019, the entire contents of each of which are incorporated herein by reference.

BACKGROUND

Myeloproliferative disorders are diseases of the bone marrow and blood. Myelofibrosis, for example, is a clonal myeloproliferative disease that is characterized by exaggerated abnormalities in megakaryocytes. The abnormal megakaryocytes are attributed primarily to dysregulation of the JAK/STAT pathway, although there is dysregulation in a number of other pathways as well. Due to the multiple pathways affected and the array of downstream effects, myelofibrosis is a complex, heterogeneous disease with many inter-related features. The abnormal megakaryocytes release excess platelets and cytokines, both pro-inflammatory and pro-fibrotic (transforming growth factor beta [TGF-β]), into the bone marrow. The pro-inflammatory cytokines lead to debilitating constitutional symptoms and exacerbate the deposition of collagen signaled by pro-fibrotic pathways. Bone marrow fibrosis is the hallmark of myelofibrosis, although diagnosis is not necessarily dependent on it. The bone marrow fibrosis is the key feature that causes the morbidity and mortality associated with the disease. The bone marrow fibrosis and inflammatory state of myelofibrosis often lead to cytopenias, extramedullary hematopoiesis (EMH), organomegaly such as splenomegaly and hepatomegaly and a myriad of constitutional symptoms.

Myelofibrosis is a serious disease in that it is both life-threatening and greatly diminishes the quality of life of the patient before it affects survival. The two most common causes of death are conversion to acute myeloid leukemia (AML) and progression of the disease. The treatment paradigm is dictated by the number of risk factors present, which then correlate with different survival rates. While allogeneic hematopoietic stem cell transplantation (HCT) can be curative, it is associated with its own morbidity and mortality, which limit its use to those eligible patients whose prognosis is worse (<5 years) than the risk of moving forward with the transplant. The remaining treatments are more palliative in nature, either due to their mechanism of action (e.g., treatments specifically focused on the anemia that is frequently associated with myelofibrosis) or due to the restricted effects that the treatment can elicit (e.g., the standard of care ruxolitinib).

Ruxolitinib, a JAK1/2 inhibitor, is approved for the treatment of myelofibrosis. JAK is a key regulator in hematopoiesis, immune regulation, growth and embryogenesis (Stahl M, Zeidan AM (2017). Management of Myelofibrosis: JAK Inhibition and Beyond. Expert Rev Hematol; 17(5): 459-477). Dysregulated JAK signaling can lead to increased thrombopoietin signaling, which is believed to be one of the causes of increased megakaryocyte production and platelets in myelofibrosis. Further, JAK signaling is implicated in the release of pro-inflammatory cytokines and growth factors that cause constitutional symptoms and splenomegaly: JAK-1 plays a role in the signaling of pro-inflammatory cytokines (e.g., IL-1, IL-16, TNF-α), the cause of systemic symptoms in myelofibrosis and JAK-2 impacts growth factors and other cytokines (e.g., IL-3, IL-5) that are believed to promote splenomegaly in myelofibrosis. Through this mechanism of action, ruxolitinib has demonstrated an ability to reduce the spleen volumes and symptoms of myelofibrosis patients, thereby improving their quality of life. Unfortunately, however, there are a number of limitations with the current use of ruxolitinib.

Ruxolitinib is considered a palliative treatment due to its lack of disease-modifying effects. It does not affect the mutant allele burden or bone marrow fibrosis (Novel Therapies for Myelofibrosis, 2017, Curr Hematol Malig Rep; 12(6): 611-624). In addition, constitutional symptoms will revert back after a week off of ruxolitinib treatment (see Tefferi A (2017); Management of Primary Myelofibrosis; UpToDate; 1-23). Next, anemia negatively impacts patient quality of life, has the highest power of predicting shortened survival, and limits access to optimal standard of care. Ruxolitinib is not a viable treatment option for some anemic patients because ruxolitinib is known to decrease red blood cell production and hemoglobin levels. Anemic patients, for example, are either not treated at all with ruxolitinib, given a lower dose of ruxolitinib leading to inadequate response, or give a full dose ruxolitinib, which typically leads to need for red blood cell (RBC) transfusions. See e.g., Haematologica. 2016 December; 101(12): e482-e484. Patients who have become dependent on RBC transfusions suffer from an even worse quality of life and prognosis.

Another unmet medical need is the lack of alternative therapies for treating myelofibrosis. This means that i) those who do not achieve an adequate response to ruxolitinib; ii) those who are intolerant to ruxolitinib; and iii) those who progress despite treatment with ruxolitinib have little or no alternative treatment options. Furthermore, approximately 75% of patients who do initially respond to ruxolitinib end up discontinuing treatment due to disease progression or toxicity.

SUMMARY

It has now been found that 2-((4S)-6-(4-chlorophenyl)-1-methyl-4H-benzo[c]isoxazolo[4,5-e]azepin-4-yl)acetamide, an inhibitor of the Bromodomain and Extra-Terminal (BET) family and referenced herein as Compound 1, is effective in treating myelofibrosis and has numerous advantages over the current standard of care, i.e., ruxolitinib.

Unlike ruxolitinib, treating myelofibrosic subjects with Compound 1 increased hemoglobin levels. This is particularly important for subjects who are also anemic. For example, patients 247 and 248 in the Exemplification section below experienced an increase in hemoglobin levels from about 8 g/dL to near normal at about 11.5 g/dL. See e.g., FIG. 5. In addition, platelet counts were normalized from about 8 g/dl to about 10.9 g/dl. See e.g., FIG. 5.

Other results showed that uncontrolled thrombocytosis could be alleviated (i.e., platelets were normalized) in a subject that was refractory to all standard of care, including the JAK inhibitor ruxolitinib, following treatment with Compound 1. See e.g., FIG. 6 and the Exemplification section below. An improvement in headaches was also found.

Further results showed transfusion dependence could be reversed following treatment with Compound 1. For example, the subject who was transfusion dependent while taking the JAK inhibitor ruxolitinib became transfusion independent after undergoing treatment with Compound 1, and remained transfusion independent for more than 24 weeks. See e.g., FIG. 5. Similar results were seen using a combination of both ruxolitinib and Compound 1. See e.g., Patients 245 and 246 in the Exemplification section below and FIG. 6, as well as the expanded data provided e.g., in FIG. 8, FIG. 10A, and FIG. 10B.

As an additional advantage, Compound 1 significantly decreased spleen size, even in subjects who were resistant to ruxolitinib. For example, prior to administration of Compound 1, Patient 245 as described below became resistant to ruxolitinib with her spleen increasing 25% in size (spleen volume was 12 cm by palpation). However, after 4 weeks of therapy with Compound 1 and ruxolitinib, her spleen size was reduced to 5 cm. See also FIG. 8, FIG. 9 FIG. 10A, and FIG. 12A which shows the spleen reduction from a Phase 2 human trial with Compound 1 and ruxolitinib.

Provided herein therefore are methods of using Compound 1, or a pharmaceutically acceptable salt thereof, alone or in combination with a JAK inhibitor such as ruxolitinib, to treat myelofibrosis.

In certain aspects, also provided herein are methods of using Compound 1, or a pharmaceutically acceptable salt thereof, alone or in combination with a JAK inhibitor such as ruxolitinib, to treat myelofibrosis in subjects with anemia.

BRIEF DESCRIPTION OF THE FIGURES

FIG. 13B illustrates the percent total symptom score improvement after treatment with Compound 1 monotherapy (Arm 1) in patients with refractory or intolerant myelofibrosis who were transfusion (Cohort 1A) or non-transfusion dependent (Cohort 1B) at the start of therapy.

FIG. 13C illustrates the Patient Global Impression of Change after treatment with Compound 1 monotherapy (Arm 1) in patients with refractory or intolerant myelofibrosis who were transfusion (Cohort 1A) or non-transfusion dependent (Cohort 1B) at the start of therapy.

FIG. 14 shows the improvement in bone marrow fibrosis from Arms 1 and 2 of the phase 2 clinical trial using Compound 1 monotherapy or as an add-on to ruxolitinib in patients with refractory or intolerant myelofibrosis who were transfusion or non-transfusion dependent at the start of therapy.

Figure 1:
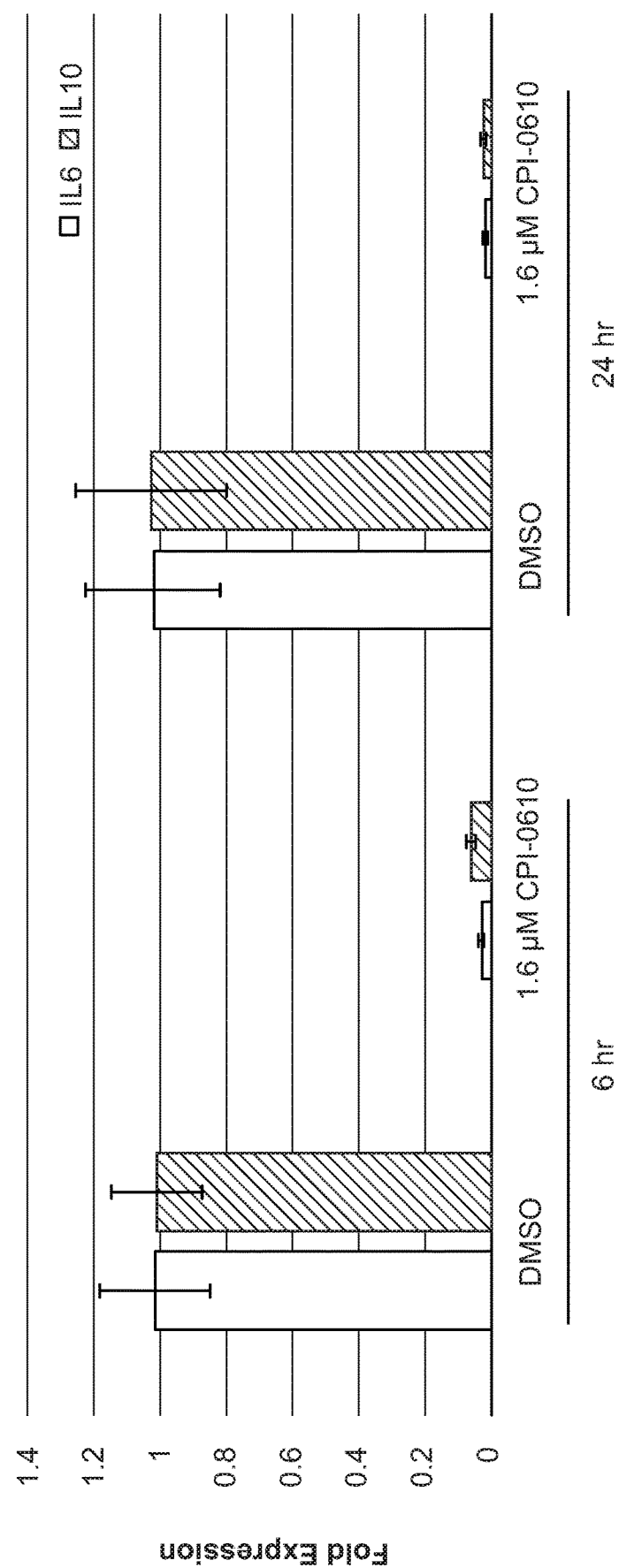
FIG. 1 shows the effects of Compound 1 on IL6 and IL10 mRNA transcript levels.

DETAILED DESCRIPTION 2-((4S)-6-(4-chlorophenyl)-1-methyl-4H-benzo[c]isoxazolo[4,5-e]azepin-4-yl)acetamide is exemplified as Compound 144 in U.S. Pat. No. 8,796,261, the entire contents of which are incorporated herein by reference. 2-((4S)-6-(4-chlorophenyl)-1-methyl-4H-benzo[c]isoxazolo[4,5-e]azepin-4-yl)acetamide is used interchangeably herein with Compound 1 and/or CPI-0610, and is represented by the following structural formula:

Crystalline forms of Compound 1 are disclosed in U.S. Pat. No. 9,969,747, the entire contents of which are incorporated by reference herein.

Compound 1 is a potent and selective small molecule designed to promote anti-tumor activity by selectively inhibiting the function of BET protein. See e.g., J. Med. Chem., 2016; Feb. 25; 59(4): 1330-9. Compound 1 is being investigated for its profound effects in treating hematological malignancies including progressive lymphoma. See e.g., U.S. Clinical Trials NCT02157636 and NCT01949883. It has now been found, however, that Compound 1 is also effective in treating myelofibrosis. To this end, for example, Compound 1 increased hemoglobin levels, normalized platelet counts, and reduced spleen size. Subjects who were previously transfusion dependent became transfusion independent after treatment.

Therefore, in a first embodiment, provided herein is a method of treating myelofibrosis in a subject comprising administering to the subject a therapeutically effective amount of 2-((4S)-6-(4-chlorophenyl)-1-methyl-4H-benzo[c]isoxazolo[4,5-e]azepin-4-yl)acetamide, or a pharmaceutically acceptable salt thereof. Also provided is the use of 2-((4S)-6-(4-chlorophenyl)-1-methyl-4H-benzo[c]isoxazolo[4,5-e]azepin-4-yl)acetamide, or a pharmaceutically acceptable salt thereof, in the manufacture of a medicament for treating myelofibrosis in a subject. Further provided is 2-((4S)-6-(4-chlorophenyl)-1-methyl-4H-benzo[c]isoxazolo[4,5-e]azepin-4-yl)acetamide, or a pharmaceutically acceptable salt thereof, for treating myelofibrosis in a subject.

The terms "subject" and "patient" may be used interchangeably, and mean a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The terms "treatment," "treat," and "treating" refer to reversing, alleviating, reducing the likelihood of developing, or inhibiting the progress of myelofibrosis, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence. Symptoms specific to myelofibrosis include, but are not limited to, abdominal discomfort, dyspnea on exertion, early satiety, fatigue, headaches, night sweats, dizziness, fever, chills, insomnia, pruritus, or bone pain.

As detailed in the Exemplification section below, Compound 1 was effective in subjects who have undergone treatment for myelofibrosis with JAK inhibitors such as ruxolitinib. Therefore, in a second embodiment, provided herein is a method of treating myelofibrosis in a subject comprising administering to the subject a therapeutically effective amount of 2-((4S)-6-(4-chlorophenyl)-1-methyl-4H-benzo[c]isoxazolo[4,5-e]azepin-4-yl)acetamide, or a pharmaceutically acceptable salt thereof, wherein the subject has previously undergone treatment with a janus kinase (JAK) inhibitor (e.g., ruxolitinib). Also provided is the use of 2-((4S)-6-(4-chlorophenyl)-1-methyl-4H-benzo[c]isoxazolo[4,5-e]azepin-4-yl)acetamide, or a pharmaceutically acceptable salt thereof, in the manufacture of a medicament for treating myelofibrosis in a subject who has previously undergone treatment with janus kinase (JAK) inhibitor (e.g., ruxolitinib). Further provided is 2-((4S)-6-(4-chlorophenyl)-1-methyl-4H-benzo[c]isoxazolo[4,5-e]azepin-4-yl)acetamide, or a pharmaceutically acceptable salt thereof, for treating myelofibrosis in a subject who has previously undergone treatment with a janus kinase (JAK) inhibitor (e.g., ruxolitinib).

As detailed in the Exemplification section below, Compound 1 was effective in subjects who have myelofibrosis, but are JAK inhibitors naïve subjects. Therefore, in a third embodiment, provided herein is a method of treating myelofibrosis in a subject comprising administering to the subject a therapeutically effective amount of 2-(((4S)-6-(4-chlorophenyl)-1-methyl-4H-benzo[c]isoxazolo[4,5-e]azepin-4-yl)acetamide, or a pharmaceutically acceptable salt thereof, wherein the subject is janus kinase (JAK) inhibitor naïve subject. Also provided is the use of 2-((4S)-6-(4-chlorophenyl)-1-methyl-4H-benzo[c]isoxazolo[4,5-e]azepin-4-yl)acetamide, or a pharmaceutically acceptable salt thereof, in the manufacture of a medicament for treating myelofibrosis in a subject who is a janus kinase (JAK) inhibitor naïve subject. Further provided is 2-((4S)-6-(4-chlorophenyl)-1-methyl-4H-benzo[c]isoxazolo[4,5-e]azepin-4-yl)acetamide, or a pharmaceutically acceptable salt thereof, for treating myelofibrosis in a subject who is a janus kinase (JAK) inhibitor naïve subject.

In a fourth embodiment, the subjects described in the first and second embodiments are characterized as progressed/relapsed to a JAK inhibitor. In a fifth embodiment, the subjects described in the first and second embodiments are characterized is refractory/resistant to a JAK inhibitor. Alternatively, as part of a fifth embodiment, the subjects described in the first and second embodiments are characterized as intolerant to a JAK inhibitor.

A subject who is characterized as progressed/relapsed is one who at one time responded to treatment with a JAK inhibitor (e.g., ruxolitinib), but who no longer responds. A subject who is characterized as refractory/resistant is one who is unresponsive or demonstrates worsening of disease while on treatment with a JAK inhibitor (e.g., ruxolitinib). In one aspect, evidence of refractoriness/resistance (including loss of response) includes no spleen size reduction or symptom improvement after 6 months of therapy, disease progression, or intolerance to ruxolitinib (i.e., platelet count <50×10$^9$/L and/or ANC <0.5×10$^9$/L despite recommended dose adjustments and interruptions per approved ruxolitinib label; bleeding; or other severe [i.e. ≥Grade 3 non-hematological] toxicity).

A subject who is characterized as intolerant is one who cannot tolerate the side effects from treatment with a JAK inhibitor (e.g., ruxolitinib) and thus has to be removed from treatment of said JAK inhibitor.

An illegible patient is defined as those patients for whom a JAK inhibitor is indicated (e.g., ruxolitinib), but the healthcare provider is reluctant to initiate treatment with the JAK inhibitor due to prior history of severe infections such as tuberculosis, PML, or skin malignancies that are known to be associated or exacerbated by the JAK inhibitor (see e.g., the approved package insert for ruxolitinib).

Compound 1 was also shown to be effective as a combination treatment with the JAK inhibitor ruxolitinib. Therefore, in a sixth embodiment, provided herein is a method of treating myelofibrosis in a subject comprising administering to the subject a therapeutically effective amount of 2-((4S)-6-(4-chlorophenyl)-1-methyl-4H-benzo[c]isoxazolo[4,5-e]azepin-4-yl)acetamide and a therapeutically effective amount of a janus kinase (JAK) inhibitor (e.g., ruxolitinib), or a pharmaceutically acceptable salt of any of the foregoing. Also provided is the use of 2-((4S)-6-(4-chlorophenyl)-1-methyl-4H-benzo[c]isoxazolo[4,5-e]azepin-4-yl)acetamide and a janus kinase (JAK) inhibitor (e.g., ruxolitinib), or a pharmaceutically acceptable salt of any of the foregoing, in the manufacture of a medicament for treating myelofibrosis in a subject. Further provided is 2-((4S)-6-(4-chlorophenyl)-1-methyl-4H-benzo[c]isoxazolo[4,5-e]azepin-4-yl)acetamide and a janus kinase (JAK) inhibitor (e.g., ruxolitinib), or a pharmaceutically acceptable salt of any of the foregoing, for treating myelofibrosis in a subject. Alternatively, as part of a sixth embodiment, the subject to be treated is a janus kinase (JAK) inhibitor naïve subject prior to treatment.

As used herein, ruxolitinib refers to the JAK inhibitor (R)-3-(4-(7H-pyrrolo[2,3-d]pyrimidin-4-yl)-1H-pyrazol-1-yl)-3-cyclopentylpropanenitrile phosphate having the following formula.

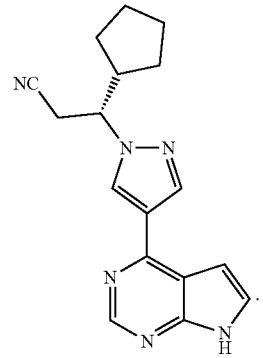 [SMILES: N#CC[C@H](C1CCCC1)n1cc(-c2ncnc3[nH]ccc23)cn1]

The term "effective amount" or "therapeutically effective amount" are used interchangeably and include an amount of a compound described herein that will elicit a desired medical response in a subject having myelofibrosis, e.g., reducing the symptoms of and/or slowing the progression of the disease.

In a seventh embodiment, the subject treated by the methods described herein (e.g., as in any one of the first through sixth embodiments) is cytopenic. Cytopenic refers to subjects in which the production of one or more blood cell types ceases or is greatly reduced. Types of cytopenia include e.g., anemia (a deficiency of red blood cells), leukopenia or neutropenia (a deficiency of white blood cells), thrombocytopenia (a deficiency in the platelets), and pancytopenia (a deficiency in all three of red blood cells, white blood cells, and platelet counts).

In an eighth embodiment, the subject treated by the methods described herein (e.g., as in any one of the first through seventh embodiments) is anemic. A subject of the present disclosure (e.g., as in any one of the first through seventh embodiments) is said to be anemic if their hemoglobin value is less than 13.5 g/dL of blood for a male subject or less than 12.0 g/dL of blood for a female subject. In some aspects, a subject (e.g., as in any one of the first through seventh embodiments) is defined herein as being anemic if their hemoglobin value is less than 10.0 g/dL. Subjects treatable by the present methods (e.g., as in any one of the first through seventh embodiments) therefore include those having hemoglobin values less than 13.0 g/dL, less than 12.5 g/dL, less than 12.0 g/dL, less than 11.5 g/dL, less than 11.0 g/dL, less than 10.5 g/dL, less than 10.0 g/dL, less than 9.5 g/dL, less than 9.0 g/dL, or less than 8.5 g/dL for male subjects and less than 11.5 g/dL, less than 11.0 g/dL, less than 10.5 g/dL, less than 10.0 g/dL, less than 9.5 g/dL, less than 9.0 g/dL, or less than 8.5 g/dL for female subjects. In others aspects, a subject (e.g., as in any one of the first through seventh embodiments) is defined herein as being anemic if their hemoglobin value ranges from 7.5 g/dL of blood to 13.5 g/dL of blood for a male subject or from 7.5 g/dL of blood to 12.0 g/dL of blood for a female subject. In others aspects, a subject (e.g., as in any one of the first through seventh embodiments) is defined herein as being anemic if their hemoglobin value ranges from 7.5 g/dL of blood to 10.5 g/dL of blood for a male subject or from 7.5 g/dL of blood to 10.5 g/dL of blood for a female subject. In others aspects, a subject (e.g., as in any one of the first through seventh embodiments) is defined herein as being anemic if their hemoglobin value ranges from 7.5 g/dL of blood to 10.0 g/dL of blood for a male subject or from 7.5 g/dL of blood to 10.0 g/dL of blood for a female subject. In others aspects, a subject (e.g., as in any one of the first through seventh embodiments) is defined herein as being anemic if their hemoglobin value ranges from 7.7 g/dL of blood to 10.7 g/dL of blood for a male subject or from 7.7 g/dL of blood to 10.5 g/dL of blood for a female subject. In others aspects, a subject (e.g., as in any one of the first through seventh embodiments) is defined herein as being anemic if their hemoglobin value ranges from 7.7 g/dL of blood to 10.0 g/dL of blood for a male subject or from 7.7 g/dL of blood to 10.0 g/dL of blood for a female subject.

In a ninth embodiment, subjects treated by the methods described herein (e.g., as in any one of the first through eighth embodiments) are thrombocytopenic. A subject of the present disclosure (e.g., as in any one of the first through eighth embodiments) is said to be thrombocytopenic if their platelet count is less than 150,000 platelets/4, of blood. Subjects treatable by the present methods (e.g., as in any one of the first through eighth embodiments) therefore include those having platelet levels less than 140,000 platelets/µL, less than 130,000 platelets/µL, less than 120,000 platelets/µL, less than 110,000 platelets/µL, less than 100,000 platelets/µL, less than 90,000 platelets/µL, less than 80,000 platelets/µL, less than 70,000 platelets/µL, less than 60,000 platelets/µL or less than 50,000 platelets/µL, alone or in combination with one or more of the hemoglobin values described above.

In a tenth embodiment, subjects treated by the methods described herein (e.g., as in any one of the first through eighth embodiments) are thrombocytemic. A subject of the present disclosure treated by the methods described herein (e.g., as in any one of the first through eighth embodiments) is said to be thrombocytemic if their platelet count is more than 450,000 platelets/µL of blood. Subjects treatable by the present methods (e.g., as in any one of the first through eighth embodiments) therefore include those having platelet levels more than 450,000 platelets/µL, more than 500,000 platelets/µL, more than 550,000 platelets/µL, or more than 600,000 platelets/µL, alone or in combination with one or more of the hemoglobin values described above. Alternatively, as part of a tenth embodiment, a subject of the present disclosure treated by the methods described herein (e.g., as in any one of the first through eighth embodiments) is said to be thrombocytemic if their platelet count is more than 400,000 platelets/µL of blood. Subjects treatable by the present methods (e.g., as in any one of the first through eighth embodiments) therefore include those having platelet levels more than 400,000 platelets/µL.

In an eleventh embodiment, the subject treated by the methods described herein (e.g., as in any one of the first through tenth embodiments) is leukopenic. A subject (e.g., as in any one of the first through tenth embodiments) is said to be leukopenic if their white blood cell (WBC) count is less than 4,000 WBCs/µl_, of blood. In certain aspects, subjects treatable by the present methods (e.g., as in any one of the first through tenth embodiments) include those having WBC counts of less than 3,500 WBCs/µL, 3,200 WBCs/µL, 3,000 WBCs/µL, or 2,500 WBCs/µL, alone or in combination with one or more of the hemoglobin and/or platelet values described above.

In a twelfth embodiment, the subject treated by the methods described herein is (e.g., as in any one of the first through eleventh embodiments) neutropenic. In one aspect, a subject of the present disclosure (e.g., as in any one of the first through eleventh embodiments) is said to be neutropenic if their neutrophil count is less than 1500 neutrophils/µl_, of blood. In certain aspects, subjects treatable by the present methods (e.g., as in any one of the first through eleventh embodiments) include those having neutrophil counts of less than 1250 neutrophils/µL, 1000 neutrophils/µL, 750 neutrophils/µL, or 500 neutrophils/µL, alone or in combination with one or more of the hemoglobin, platelet, and/or WBC values described above.

Myelofibrosis is often associated with an enlarging of the spleen. Enlarging of the spleen can result in a feeling of fullness, indigestion, and a loss of appetite. In a thirteenth embodiment, subjects treatable by the present methods (e.g., as in any one of the first through twelfth embodiments) include those having an enlarged spleen or liver.

In a fourteenth embodiment, subjects treatable by the present methods (e.g., as in any one of the first through thirteenth embodiments) may also be experiencing one or more additional symptoms. These symptoms include, but are not limited to, abdominal discomfort, dyspnea on exertion, early satiety, fatigue, headaches, night sweats, dizziness, insomnia, pruritus, or bone pain.

In a fifteenth embodiment, subjects treated by the present methods (e.g., as in any one of the first through fourteenth embodiments) are transfusion dependent prior to treatment with Compound 1. In some aspects, "transfusion dependent" means that a subject requires red blood cell (RBC) transfusions in order to maintain an acceptable level of hemoglobin. An acceptable level of hemoglobin is determined by those skill in the art and can range from e.g., from 13.5 to 17.5 g/dL of blood for men and from 12.0 to 15.5 g/dL of blood in women. It will be understood that subjects undergoing treatment with Tux may have lower hemoglobin levels than those described above and still be deemed an "acceptable" level in order for treatment to continue.

In a sixteenth embodiment, subjects treated by the present methods (e.g., as in any one of the first through fifteenth embodiments) experience a reduction in spleen size. In one aspect, the reduction comprises a 10% or more (e.g., a 15% or more, a 20% or more, a 25% or more, a 30% or more, a 35% or more, a 40% or more, a 45% or more, a 50% or more, a 55% or more, a 60% or more, or a 65% or more reduction in spleen volume from baseline. In another aspect, the reduction comprises from a 10% to a 65% reduction in spleen volume from baseline.

In a seventeenth embodiment, subjects treated by the present methods (e.g., as in any one of the first through sixteenth embodiments) experience a reduction in headaches.

In an eighteenth embodiment, subjects treated by the present methods (e.g., as in any one of the first through seventeenth embodiments) have a reduction in the number of blood transfusion.

In a nineteenth embodiment, subjects treated by the present methods (e.g., as in any one of the first through eighteenth embodiments) experience a normalization of platelets.

In a twentieth embodiment, subjects treated by the present methods (e.g., as in any one of the first through nineteenth embodiments) experience an increase in hemoglobin values.

In a twenty-first embodiment, subjects treated by the present methods (e.g., as in any one of the first through twentieth embodiments) experience an improvement in bone marrow fibrosis as determined e.g., by the bone marrow fibrosis grading scale (see Thiele J et al., Haematologica, 2005, 90, 1128). In one aspect, an improvement is defined as at least one grade improvement in the bone marrow fibrosis/reticulin grading compared to baseline.

In a twenty-second embodiment, subjects treated by the present methods (e.g., as in any one of the first through twenty-second embodiments) experience a reduction in pro-inflammatory cytokines such as e.g., CRP, IL-8, and/or IL-18.

The compounds of the methods described herein can be formulated as pharmaceutical compositions and administered to a subject, such as a human, in a variety of forms adapted to the chosen route of administration. Typical routes of administering such pharmaceutical compositions include, without limitation, oral, topical, buccal, transdermal, inhalation, parenteral, sublingual, rectal, vaginal, and intranasal. The term parenteral as used herein includes subcutaneous injections, intravenous, intramuscular, intrathecal, intrasternal injection or infusion techniques. Methods of formulating pharmaceutical compositions are well known in the art, for example, as disclosed in "Remington: The Science and Practice of Pharmacy," University of the Sciences in Philadelphia, ed., 21st edition, 2005, Lippincott, Williams & Wilkins, Philadelphia, Pa.

Pharmaceutical compositions of the invention can be prepared by combining a compound of the methods described herein with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Thus, the present compounds of the methods described herein may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition. In one aspect, however, when used as a monotherapy (i.e., without a JAK inhibitor such as ruxolitinib) Compound 1, or a pharmaceutically acceptable salt thereof, may be formulated at a dose of from 50 mg to 500 mg for e.g., administration once, twice, or three times daily. For example, in monotherapies, Compound 1 may be administered at a dosage of from 50 mg to 300 mg/day, from 75 mg to 300 mg/day, from 100 mg to 300 mg/day, from 150 mg to 250 mg/day, or at 150 mg/day, 175 mg/day, 200 mg/day, 225 mg/day, or 250 mg/day. In other aspects, when used in combination with a JAK inhibitor such as ruxolitinib, Compound 1, or a pharmaceutically acceptable salt thereof, may be formulated at a dose of from 50 mg to 500 mg for e.g., administration once, twice, or three times daily. For example, in combination therapies, Compound 1 may be administered at a dosage of from 50 mg to 300 mg/day, from 75 mg to 300 mg/day, from 100 mg to 300 mg/day, from 100 mg to 200 mg/day, or at 100 mg/day, 125 mg/day, 150 mg/day, 175 mg/day, or 200 mg/day.

EXEMPLIFICATION

Compound 1 can be obtained following the procedures described in U.S. Pat. No. 8,796,261 and WO 2015/195862, both of which are incorporated herein by reference.

Inhibitory Effect on Cytokine Release In Vitro

Compound 1 was assessed for its ability to suppress the expression of NF-κB target genes in two experiments. In one experiment, THP-1 acute leukemia cell lines were exposed to lipopolysaccharide treatment and then Compound 1 for 16 hours. IL6 release from the THP-1 acute leukemia cells was inhibited, with an $IC_{50}$ of 0.069 µM. In the other experiment, the ability of Compound 1 to suppress both IL6 and IL10 expression in TMD8 ABC-DLBCL cells was investigated (data on file). TMD8 cells were incubated with DMSO or 1.6 µM Compound 1 for 6 or 24 hours. RNA was then extracted from the cells and quantified using qRT-PCR. As shown in FIG. 1, Compound 1 substantially suppressed mRNA transcription of both IL6 and IL10 after 6 and 24 hours of treatment.

Effect of Compound 1 as a Single Agent on Megakaryocyte Differentiation

Figure 2:
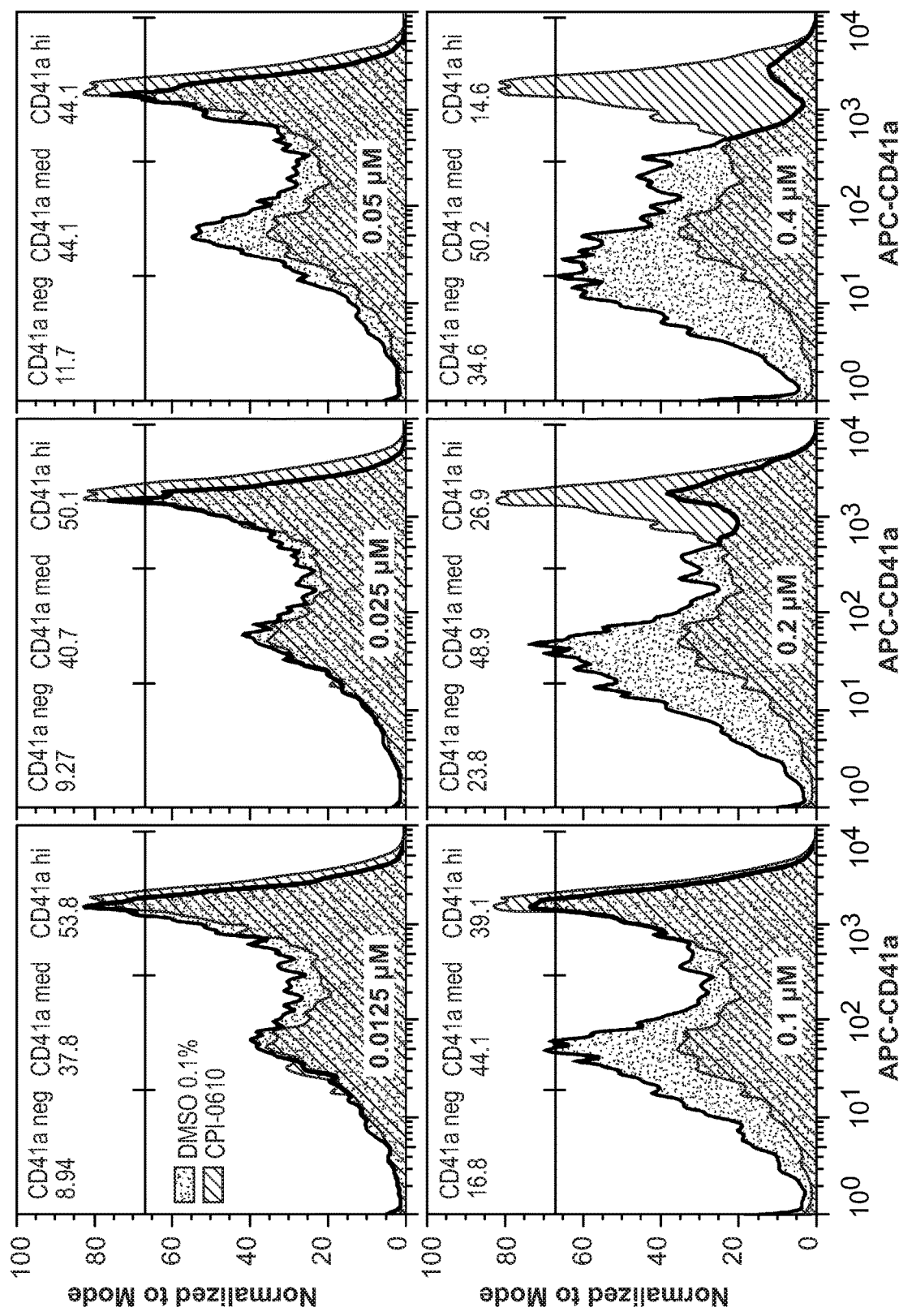
FIG. 2 depicts histograms of Compound 1 effect on megakaryocyte differentiation.

The effects of Compound 1 on megakaryocyte differentiation and proliferation were evaluated using CD34+ cells isolated from healthy donor bone marrow (data on file). The CD34+ cells were grown in megakaryocyte differentiation serum-free stem cell differentiation base medium with a megakaryocyte-driving cytokine cocktail for 14 days with DMSO or Compound 1 at concentrations ranging from 3 nM to 500 nM. The cells were then stained for CD34 (progenitor marker), CD45 (leukocyte marker) and CD41a (mature megakaryocyte marker) and assessed by FACS for viability and marker expression. CD41a expression and cell size were used as markers of megakaryocyte differentiation. Compound 1 reduced the number of cells with high CD41a expression in a concentration-dependent manner. The shift from high to low CD41a expression began at approximately 50 nM, with pronounced effects observed at 200 to 500 nM, as shown in FIG. 2. The loss of CD41a-high-expressing cells suggests impaired megakaryocyte differentiation and loss of mature megakaryocytes.

Effects of Compound 1 Alone and in Combination with Ruxolitinib on Megakaryocyte Differentiation and Proliferation In a similar experiment, CD34+ cells that were isolated from the bone marrow of two healthy donors were incubated for 10 days in megakaryocyte differentiation media with DMSO; Compound 1 alone, at a concentration of 30 to 500 nM; ruxolitinib alone at concentration of 8 to 1000 nM; or Compound 1 in combination with ruxolitinib at the same concentrations they were tested alone (data on file). The cells were then harvested for FACS analysis with live/dead stain and gating with CD34 (progenitor marker) and CD41a and CD42b (mature megakaryocyte markers). While Compound 1 showed limited effects on overall viability (percent of live cells by live/dead stain), it demonstrated potent effects on overall cell proliferation (total live count) and megakaryocyte differentiation (percent of cells double positive for CD41a and CD42b), which led to an overall loss of live mature megakaryocytes (mean $EC_{50}$ of 28 nM; Table 1).

Figure 3:
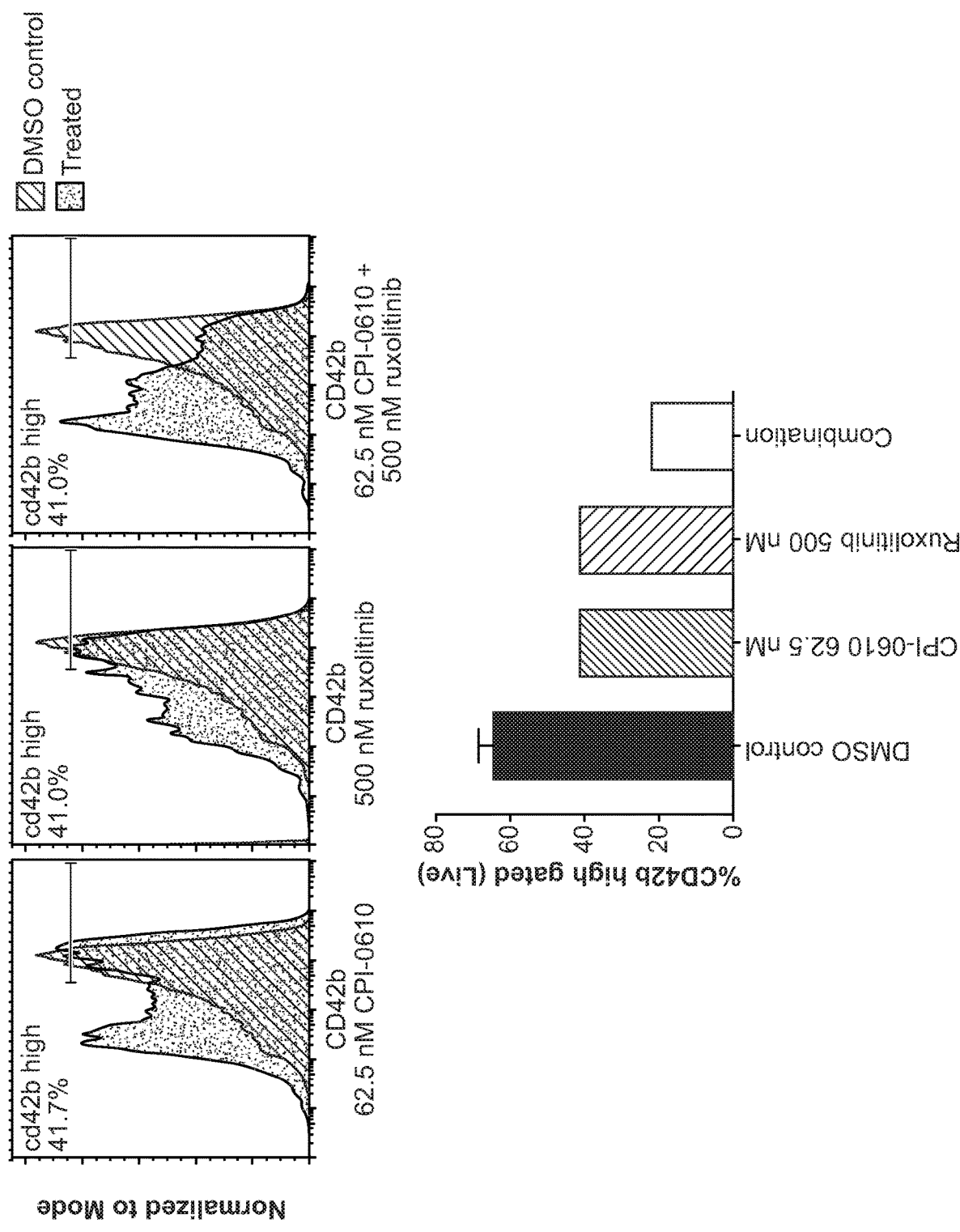
FIG. 3 represents the histograms and quantitation of effects on mature megakaryocyte marker CD42b after Treatment with Compound 1 and ruxolitinib for 10 days in stem-cell derived megakaryocyte cultures from healthy donor 2 where the grey histrogram is DMSO treated sample, blue histogram is Compound 1 treated sample, and CD42b high calculations refer to the Compound 1-treated samples.

In contrast to Compound 1, ruxolitinib exerted effects on megakaryocyte differentiation at a similar concentration that killed the progenitor cells (mean $EC_{50}$ values of 526 and 644 nM, respectively; Table 1), suggesting the inhibitory effects of ruxolitinib on megakaryocytes are based on its cytotoxicity. When serial dilutions of Compound 1 were combined with serial dilutions of ruxolitinib, an additive inhibitory effect was observed on megakaryotcyte differentiation (FIG. 3). A similar additive effect was seen on overall cell proliferation where the mean $EC_{50}$ for Compound 1 decreased from 38 to 17 nM (extrapolated), below the lowest dose tested in the presence of 250 nM ruxolitinib, indicating that concentrations of Compound 1 and ruxolitinib near their $IC_{50}$ values for megakaryocyte differentiation and proliferation were effective at reducing the quantity of the other agent needed to elicit the same effect.

TABLE 3

Compound 1 EC50 values following 10 days of treatment of CD34+ cells

| | Compound 1 $EC_{50}$ (nM) | | | Ruxolitinib $EC_{50}$ (nM) | | |
|---|---|---|---|---|---|---|
| Parameter | Donor 1 | Donor 2 | Mean | Donor 1 | Donor 2 | Mean |
| Viability | 300 | >500 | 400 | 676 | 611 | 644 |
| Total live count | 43 | 32 | 38 | 288 | 259 | 274 |
| Megakaryocyte differentiation | 60 | 131 | 96 | 517 | 535 | 526 |
| Megakaryocyte live count | 26 | 29 | 28 | 312 | 258 | 285 |

Reduction in Cytokine Levels in Peripheral Blood

Figure 4:
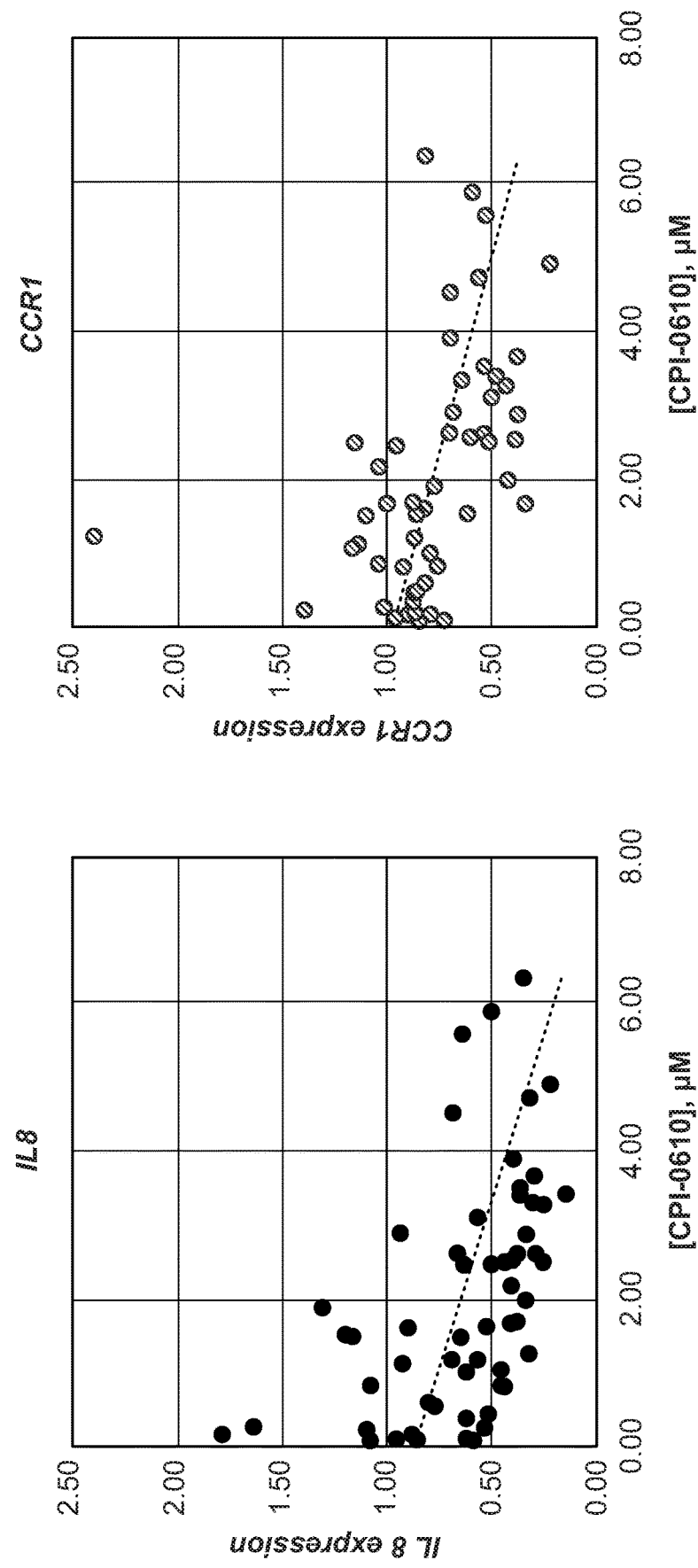
FIG. 4 shows the repression of BET-target genes IL8 and CCR1 in circulating blood 2 hours post-dose as a function of the plasma concentration of Compound 1.

A panel of selected BET target genes (CCR1, CCR2, IL8, FN1, CSF1R and THBS1) was evaluated in peripheral blood samples from patients participating in the Compound 1 Phase 1 clinical studies, in order to determine the relationship between systemic exposure of Compound 1 and suppression of these BET inhibitor-sensitive genes. Gene expression analysis, along with the Compound 1 plasma concentration versus time data, shows that there is a time- and concentration-dependent relationship. Consistent with non-clinical data, Compound 1-induced changes in expression were most consistently observed for IL8 and CCR1 at 2 hours post treatment, indicating the rapid effects of BET inhibition on transcription. Examples of the exposure-response relationships for CCR1 and IL8 are presented in FIG. 4. The data shown includes samples taken from patients with lymphoma who were treated with Compound 1 in Study 0610-01. Gene expression values were normalized to those measured at a single time point pre-treatment (100%). This data demonstrated the rapid on-target effects of BET inhibition on key pro-inflammatory genes and supports the use of this clinical biomarker assay.

Initial Human Clinical Data Set

Clinical Signs Overview of Activity in Patients with Myelofibrosis

Four patients with myelofibrosis were enrolled in a human trial that demonstrated clinical benefit which extended at least 6 months. Two myelofibrosis patients to enroll (Patients 245 and 246) received Compound 1 in combination with ruxolitinib and received 18 treatment cycles (11 months of treatment). The other two patients to enroll (Patients 247 and 248) received 10 cycles of Compound 1 as monotherapy (6 months of treatment). All four patients experienced a reduction in their constitutional symptoms along with a decrease in spleen volume and an increase in hemoglobin. One of the patients who was transfusion dependent at study entry became transfusion independent (defined as >12 weeks without the need for a red blood cell (RBC) transfusion. Indeed, 7 months had elapsed since their last transfusion.

All four patients experienced an increase in their hemoglobin levels with multiple treatment cycles with Compound 1. In addition, one of the patients who entered the study with uncontrolled thrombocytosis (baseline platelets were 895× $10^9$/L) experienced a normalization of their platelet counts within the first month of monotherapy treatment with Compound 1. The patient's platelet counts remained normal for more than 20 weeks. This patient's thrombocytosis was also accompanied by severe headaches requiring multiple hospital admission. Following treatment with Compound 1, however, the patient's headaches were resolved. Brief narratives for all four patients treated for at least 6 months are presented below.

Combination Therapy Arm

Patient 245, a 66 year-old female was diagnosed with myelofibrosis in May 2014, remained treatment naïve until January 2016 when she initiated treatment with ruxolitinib 15 mg twice daily (BID). Panobinostat was added in February 2016 and discontinued in March 2017, due to the development of anemia. From March 2017, while on ruxolitinib alone, the patient became resistant to ruxolitinib, with her spleen increasing 25% in size.

At entry into the study with Compound 1, her spleen volume by MRI was 1404 cc and was 12 cm by palpation. The patient presented with early satiety, night sweats, and dyspnea at the start of the study. Within 4 months of treatment with Compound 1, 125 mg QD and ruxolitinib 15 mg BID, the patient had resolution of early satiety; her spleen was 5 cm by palpation and her liver was no longer palpable. The lowest spleen volume by MRI was 1144 cc, a 19% reduction, at the 6-month MM. The dose of ruxolitinib was reduced on Cycle 10 to 7.5 mg BID to address decreasing platelet count. Her platelets counts gradually improved following the dose reduction of ruxolitinib and remained below the protocol-specified criteria of 100×$10^9$/L for two treatment cycles to permit a dose increase in Compound 1.

Patient 246 is a 53 year-old female who was diagnosed with myelofibrosis in 2009. During 2002 and 2006, the patient cycled between epoetin alfa, lenalidomide and thalidomide then received lenalidomide for 7 years until 2013. She required RBC transfusions during 2013 and initiated interferon in 2014, which allowed her to become transfusion independent. Interferon was discontinued almost a year later due to fatigue. The patient remained transfusion independent and without further treatment until late 2016 when they once again became transfusion dependent. Ruxolitinib 5 mg BID was started in January 2017. Ruxolitinib was increased to 10 mg BID in April 2017, but the patient remained transfusion dependent and symptomatic. She was considered ruxolitinib resistant due an increasing spleen size and exacerbated symptoms (extreme fatigue, shortness of breath, distress on exertion, occasional nausea and night sweats) while on ruxolitinib therapy.

Figure 5:
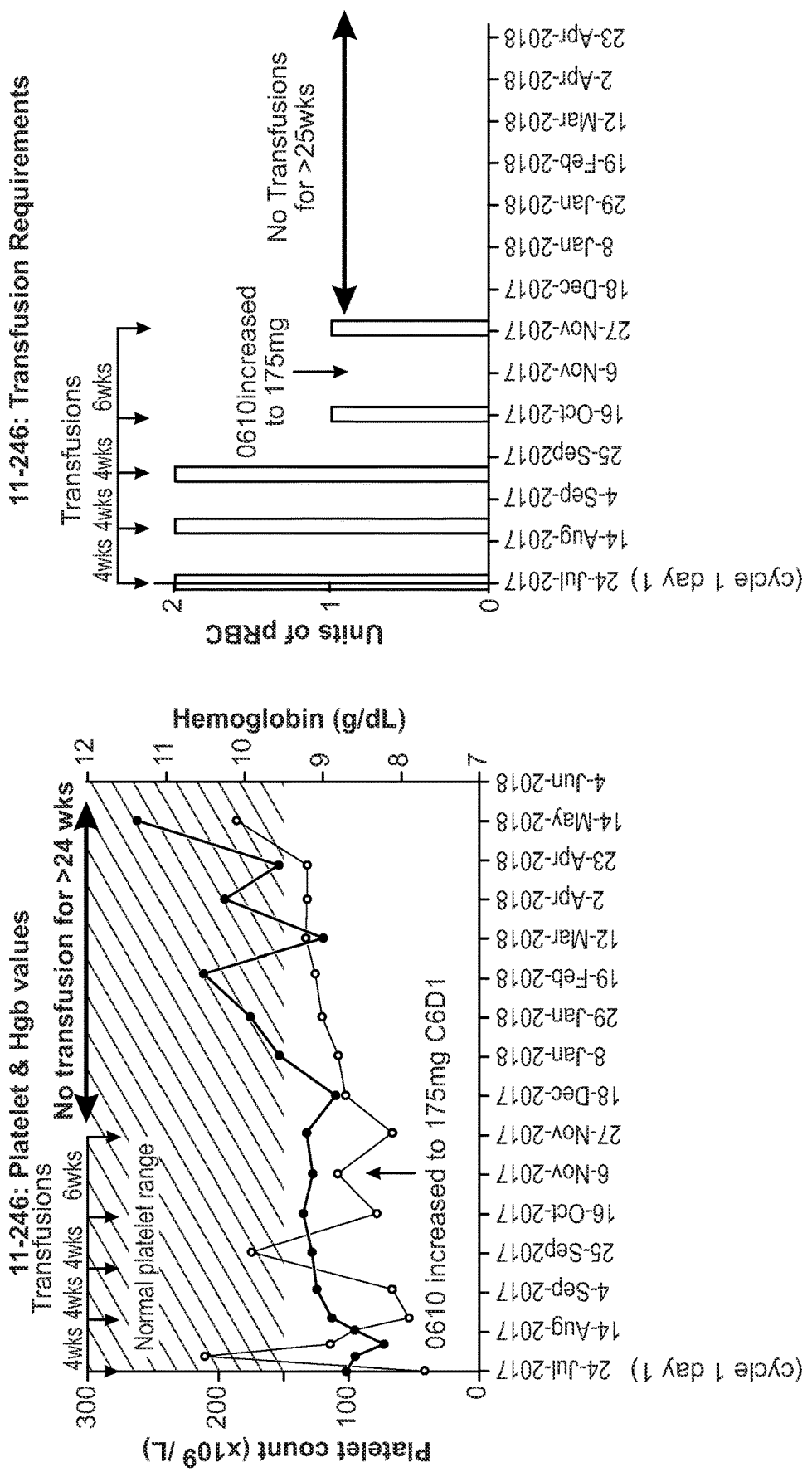
FIG. 5 shows the changes in hemoglobin levels and transfusion requirements in a combination arm of Compound 1 and ruxolitinib.

When Patient 246 initiated combination treatment with Compound 1 125 mg QD and ruxolitinib 10 mg BID her spleen volume was 607 cc by MRI and 2 cm by palpation and she required regular transfusions (2 units of RBC every 3-4 weeks). The dose of Compound 1 was titrated up to 175 mg QD after five treatment cycles and within 7 months of combination therapy, the patient had become transfusion independent (defined as >12 weeks without a transfusion and hemoglobin >8 g/dL; see FIG. 5), which has been maintained for >30 weeks (most recent hemoglobin measurement was 10.9 g/dL). She has also experienced a clinically meaningful improvement in her associated constitutional symptoms (fatigue and dyspnea) and has had an incremental decrease in spleen volume, achieving a 37% reduction in spleen volume by Cycle 12 (380 cc).

Monotherapy Arm

Patient 247 is a 46 year-old female who was diagnosed with myelofibrosis in April 2014. In 2009, it was suspected that the patient had essential thrombocytosis (ET) for which she received hydroxyurea treatment from April 2009 to December 2017. The patient also received one month of epoetin alpha in 2015, three months of imetelstat in 2016 and four months of pembrolizumab in 2017. Ruxolitinib was administered from October 2015 to May 2016. Ruxolitinib was discontinued due to worsening symptomatic splenomegaly, anemia, leukocytosis, and thrombocytosis.

Figure 6:
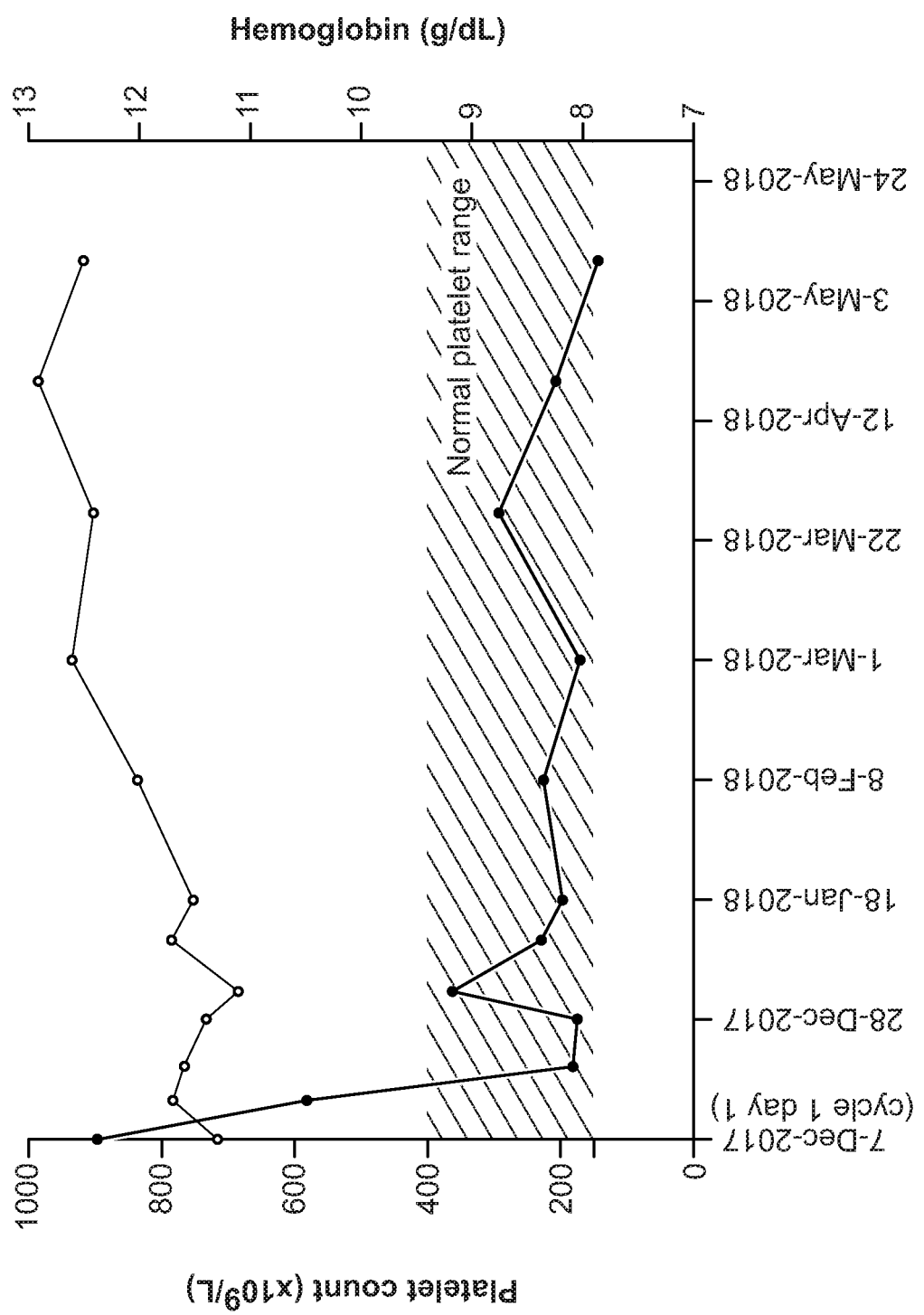
FIG. 6 shows the change in platelet and hemoglobin levels in patient 247 of the monotherapy arm.

Upon entry into the study with Compound 1, Patient 247 had a spleen volume of 858 cc by MIII and 5 cm by palpation and a host of constitutional symptoms, including: abdominal discomfort, dyspnea on exertion, early satiety, fatigue, headaches, night sweats, dizziness, insomnia, pruritus, and bone pain. The patient also presented with uncontrolled thrombocytosis at study entry (platelet count of $895 \times 10^9$/L at baseline) despite hydroxyurea. In addition, the patient had experienced persistent and debilitating headaches that required multiple hospital admissions for pain control. Their platelets were normalized after receiving their first two weeks of Compound 1 monotherapy ($183 \times 10^9$/L) and have remained within the normal range for the remainder of the time they have been on study (see FIG. 6). Within 2 months on Compound 1 monotherapy, the patient's severe headaches had resolved; their night sweats were less frequent; and a 37% reduction in symptoms was assessed by the Myeloproliferative Neoplasm Symptom (MNS) score. Their ECOG performance score decreased from 2 to 1 after two treatment cycles with CPI-0610 and a 25% decrease in spleen volume (640 cc) was assessed by MRI after 8 treatment cycles, the most recent measurement.

Patient 248, a 76 year-old male who was diagnosed with myelofibrosis in September 2011 was treated with fresolemunib (December 2011 to October 2012) and itacitinib (December 2012 to July 2014). Ruxolitinib 5 mg BID was initiated in January 2015 and increased to 15 mg BID in December 2015. Ruxolitinib was discontinued in September 2016 because the patient was experiencing generally worsening fatigue, anemia and thrombocytopenia. Subsequent to ruxolitinib treatment, the patient received imetalstat from June 2016 through March 2017, followed by pembrolizumab from June to October 2017.

Upon entry into the study with Compound 1, the patient had a spleen volume of 1148 cc by MRI and 5 cm by palpation. Their constitutional symptoms at study entry included fatigue, early satiety, and difficulty concentrating. The patient did not tolerate the 225 mg QD starting dose of Compound 1 (he experienced nausea, diarrhea, malaise and dizziness), requiring dose interruption after the first 5 doses of Cycle 1. The patient was reinitiated with a reduced Compound 1 dose of 175 mg at the beginning of Cycle 2, which has been tolerated for the remaining time on study (>6 months). While the patient's spleen has shown minimal change through palpation a spleen volume reduction of 11% (1023 cc) was measured by MRI after 3 months on treatment with Compound 1. Their MNS score improved 19% after 2 months on the 175 mg QD dose and after 6 months of Compound 1 treatment his bone marrow fibrosis grade decreased from MF-2 at baseline to MF-1 based on a local pathologist's assessment.

Human Phase 2 Clinical Data Set

A Phase 2 study of Compound 1 in subjects with myelofibrosis (MF) was conducted. Three treatment arms were studied:

Arm 1=monotherapy with Compound 1 in patients (pts) who are no longer on Rux and are with refractory, intolerant, or ineligible. In this arm patients were further stratified based on transfusion dependence status [transfusion dependent (TD), defined as an average of ≥2 units per month over 12 wks, or non-TD cohorts]. Primary endpoint: spleen volume response (SVR) for non-TD cohorts or TD to transfusion independence (TI, no transfusion for consecutive 12 wks) conversion for TD cohorts; secondary endpoints: change in total symptom score (TSS) per MFSAF v4.0, patient global impression of change (PGIC), safety and PK; additional endpoints: changes in proinflammatory Ck levels, BM morphology and mutant allele burden.

Arm 2=combination add-on treatment of Compound 1 in patients (pts) who are already being administered Rux. In this arm patients were further stratified based on transfusion dependence status [transfusion dependent (TD), defined as an average of ≥2 units per month over 12 wks, or non-TD cohorts]. The starting dose of Compound 1 was 125 mg daily on days 1-14 of a 21-day cycle in both arms. Primary endpoint: spleen volume response (SVR) for non-TD cohorts or TD to transfusion independence (TI, no transfusion for consecutive 12 wks) conversion for TD cohorts; secondary endpoints: change in total symptom score (TSS) per MFSAF v4.0, patient global impression of change (PGIC), safety and PK; additional endpoints: changes in proinflammatory Ck levels, BM morphology and mutant allele burden.

Arm 3=combination treatment with Compound 1 and Rux in patients (pts) who have not previously been administered a JAK inhibitor, i.e., JAK inhibitor treatment naïve. In this arm, key eligibility criteria of included JAKi naïve myelofibrosis (MF) patients (pts) with Dynamic International Prognostic Scoring (DIPSS) score int-1 or higher, ECOG performance status ≤2, platelet counts (PLT) ≥100×109/L, peripheral blood blast count <10%, anemia (hemoglobin <10 g/dL), ≥5 cm palpable spleen, ≥2 symptoms measurable (score ≥3) or a total symptom score (c using the MFSAF v4.0. Primary endpoint: spleen volume response (SVR); key secondary endpoints: change in TSS, safety and PK; additional endpoints: changes in proinflammatory cytokine (Ck) levels, BM morphology and mutant allele burden.

Figure 7:
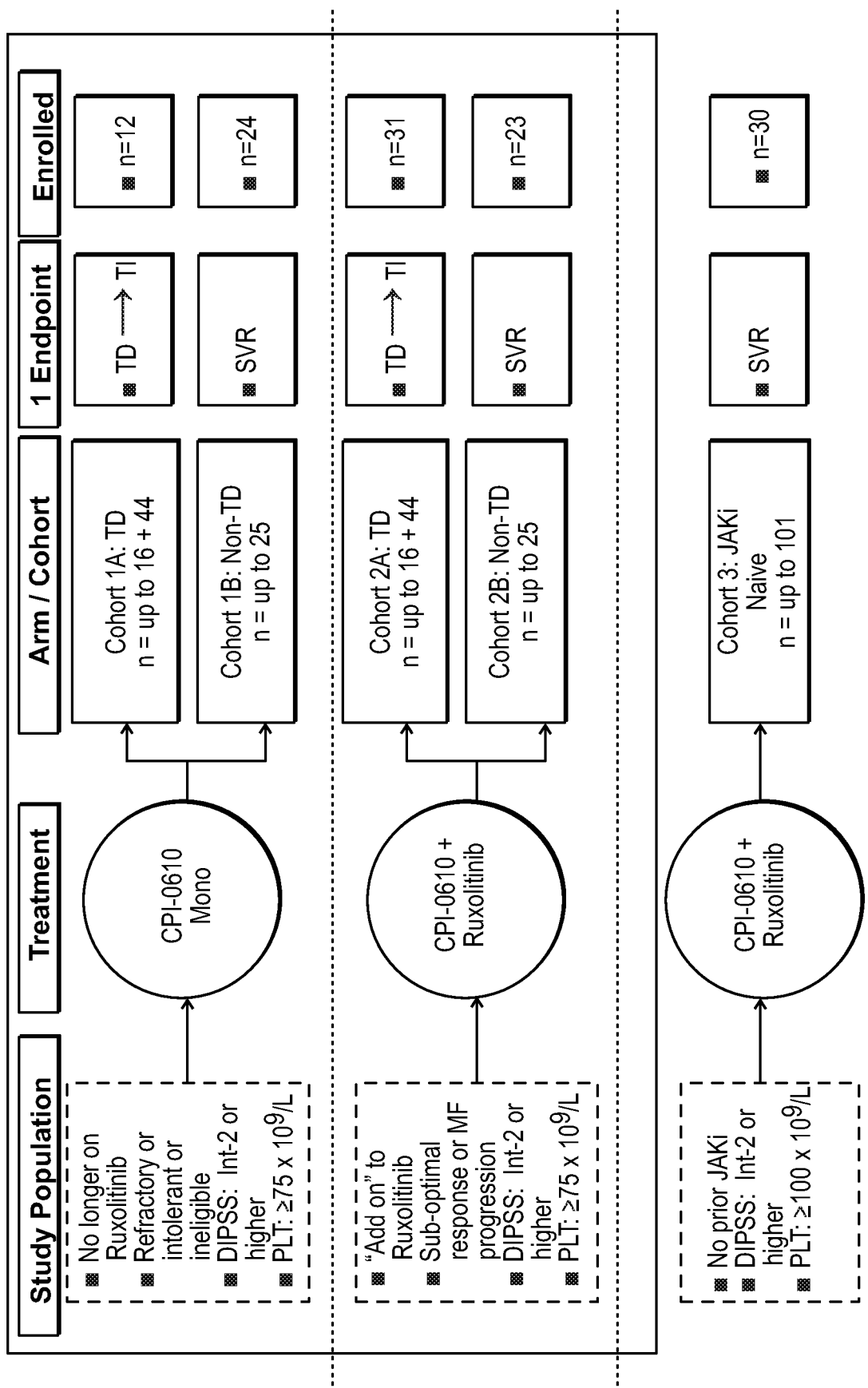
FIG. 7 shows the study design for a Phase 2 trial with Compound 1 and Compound 1 with ruxolitinib in patients with myelofibrosis.

The starting dose of Compound 1 was 125 mg given orally, once daily for 2 weeks on/1 week off in a 21-day dosing cycle. Two separate time points for data analysis occurred for at least Arms 1 and 2 and are discussed below: one at approximately 12 weeks of treatment (first assessment of spleen volume by MIII or CT and every 12 weeks thereafter) and another at approximately 24 weeks of treatment (first assessment of bone marrow biopsy and every 24 weeks thereafter). Patients were added to the study following the first time point. An overview of the study profile is shown in FIG. 7.

Time Point 1:

Arm 1 and Arm 2—Compound 1 as Monotherapy or Add-On to Ruxolitinib in Patients with Refractory or Intolerant Advanced Myelofibrosis Demographics and results are as follows: At baseline, median age: 69 years (41-88), gender: 28 (58%) male, ECOG ≤1: 45 (94%) patients, primary MF: 33 (69%) patients, DIPSS score high: 10 (21%) patients, median platelet: 199×109/L (77-895), 34 (71%) patients with Hgb <10 g/dL, median spleen volume: 2183 cc (123-3909), median TSS: 17.6 (1.4-56), 46 (96%) patients had ≥1 JAK2/MPL/CALR mutations, and 34 (71%) patients had HMR (high molecular risk) mutations. 33 (69%) patients on treatment for ≥12 wks, 4 on treatment for >18 months.

Figure 8:
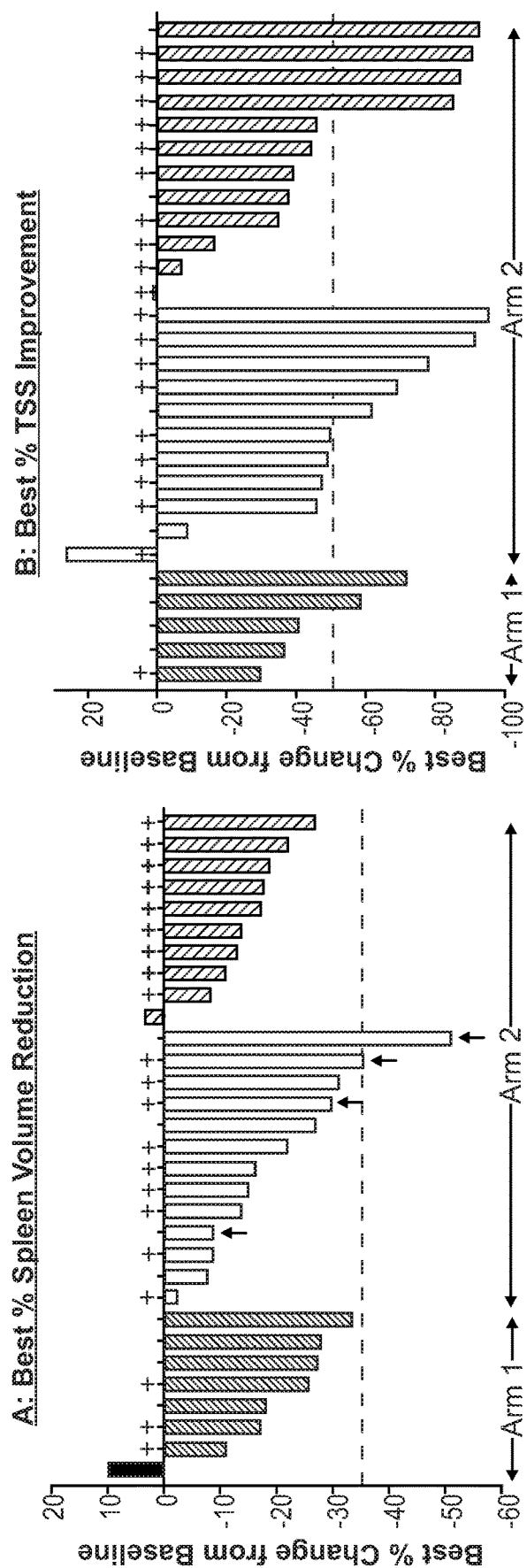
FIG. 8 shows the spleen reduction volume improvement from a Phase 2 human trial using Compound 1 monotherapy or as an add-on to ruxolitinib in myelofibrosis patients (panel A) as well as the total symptom score (TSS) improvement from a Phase 2 human trial using Compound 1 monotherapy or as an add-on to ruxolitinib in myelofibrosis patients (panel B).

Spleen volume reduction observed in 29 of 31 (94%) patients (median best change: −17% [range: −50.7, 10.2]) (FIG. 8, panel A). TSS improvement was reported in 26 of 28 (93%) patients (median best change: −46.4% [range: −95.3%, 27%]), 11 (39%) patients with ≥50% TSS improvement (FIG. 8, panel B). PGIC improvement score in 28 of 33 (85%) patients; 21 (64%) reported much or very much improved scores. Increase in hemoglobin by 1.5 mg/dL post-baseline observed with both Compound 1 monotherapy (4 of 8, 50%) and Compound 1 with ruxolitinib (4 of 25, 16%)). Improvement in BM fibrosis and/or reticulin by ≥1 Gr reported in 7 of 12 (58%) evaluable patients with baseline and 1 post-baseline biopsy and as early as 6-months of Compound 1 treatment. 4 TD patients in Arm 2 treated with Compound 1 with ruxolitinib converted to TI-2 of whom are TI for >36 wks, no longer anemic, and showed spleen volume reduction, improvement in symptom and BM fibrosis; 12 additional patients are being monitored for potential TI conversion. 41 patients remain active on treatment and 7 patients discontinued, including 1 patient, initially transplant ineligible, underwent stem cell transplantation after 6 cycles of Compound 1 with ruxolitinib treatment. Most common (≥20%) treatment-emergent adverse events (TEAE) of any Gr include diarrhea, nausea, cough and upper respiratory tract infection. Most common (≥5%) ≥3 Gr TEAE include anemia (8.3%) and thrombocytopenia (8.3%, asymptomatic, non-cumulative and generally reversible).

This data indicates that Compound 1 alone or "add-on" to ruxolitinib is generally well-tolerated and provides clinical benefits in MF patients with inadequate responses or who are refractory to ruxolitinib. Improvement in BM fibrosis and anemia responses indicate the potential for meaningful disease modification.

Figure 9:
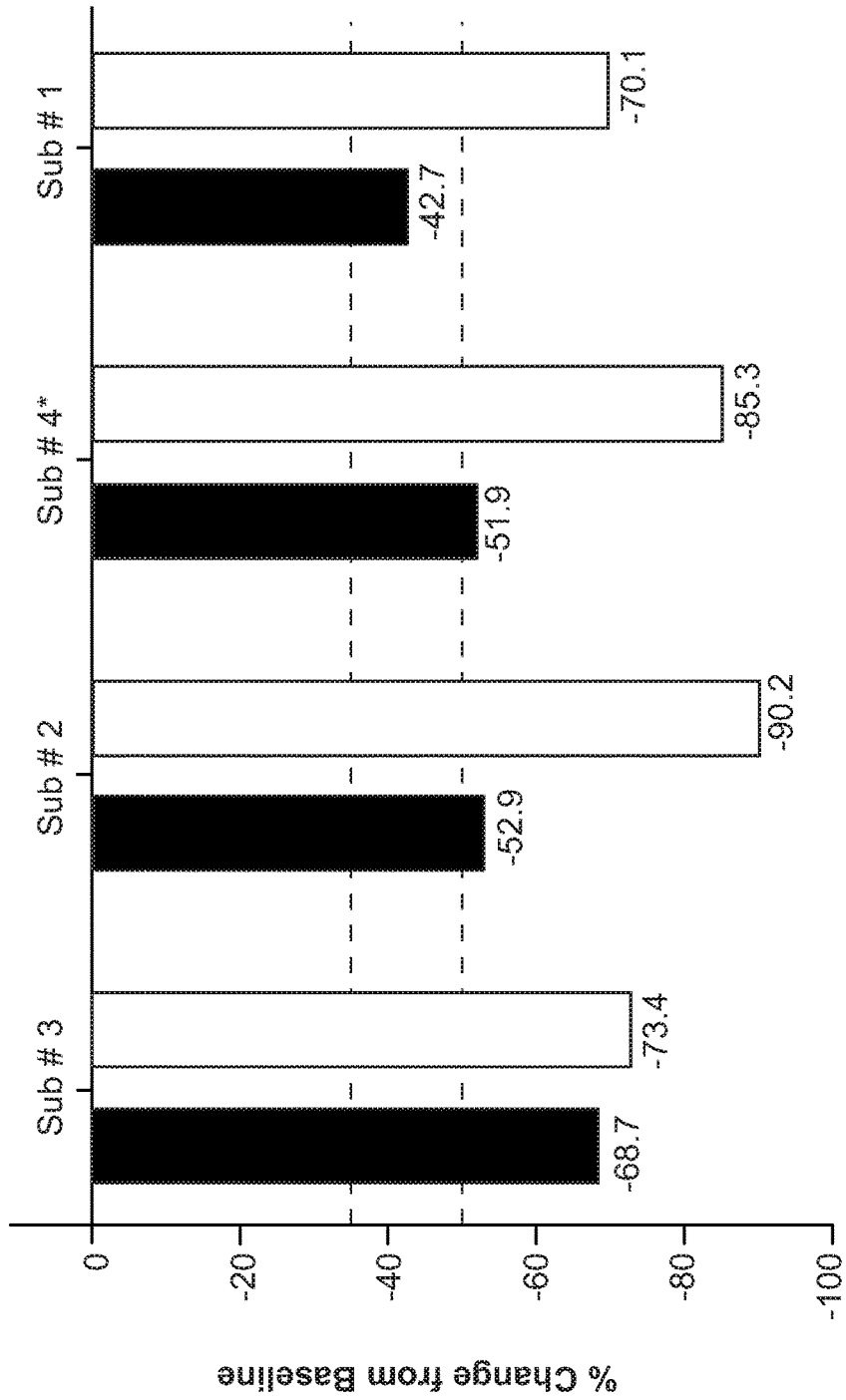
FIG. 9 shows the spleen reduction volume and total symptom score (TSS) improvement from a Phase 2 human trial using Compound 1 and ruxolitinib in JAK inhibitor treatment naïve myelofibrosis patients.

Arm 3—Compound 1 and Ruxolitinib in JAK Inhibitor Treatment Naïve Myelofibrosis Patients Demographics and results are as follows: Baseline median age: 71 years (52-76), gender: 8 male (72.7%), ECOG ≤1: 10 (90.9%) patients, primary MF: 8 (72.7%) patients, DIPSS score: int-1/int-2/high: 2/7/2 patients, median platelet: 368× 109/L (112-951), 9 (81.8%) patients with hemoglobin <10 g/dL, median spleen volume: 1379 cc (580-2807), median TSS: 11.8 (4.1-17), driver mutations: 11 (100%) with ≥1 JAK2/MPL/CALR mutations, HMR (high molecular risk) mutations: 6 (56%) patients, and ≥3 mutations: 4 (36%) patients. All 4 (100%) patients on treatment for ≥12 weeks achieved ≥35% spleen volume reduction (median: −52.4%, [range −68.7%, −42.7%]) and all 4 patients (100%) achieved ≥50% improvement in TSS (median best change: −79.35% [range −90.2%, −70.1%]). See FIG. 9, where * is data post cut off-date. A reduction of proinflammatory Ck, including IL-18 and CRP, was also observed. Safety data from the first 6 patients who received treatment for at least 1 cycle were reviewed: no DLTs or grade ≥3 thrombocytopenia was observed. The most common treatment-emergent adverse events (TEAE) observed in ≥2 patients include anemia (1 grade 3), fatigue (all ≤grade 2), and non-cumulative reversible thrombocytopenia (all ≤grade 2).

Overall, the combination of Compound 1 and ruxolitinib was generally well-tolerated demonstrating that the safety of this combination is acceptable in JAKi naïve MF patients with anemia. Early clinical activity was observed with the combination: all 4 evaluable patients achieved both ≥35% SVR and ≥50% improvement in TSS as early as 3 months after treatment. Available data in JAKi naïve anemic MF patients, a population with poor prognosis, along-with additional information on reduction in pro-inflammatory Ck and BM fibrosis improvement in Compound 1 treated patients in ruxolitinib refractory MF, collectively indicate that addition of Compound 1 to ruxolitinib could have disease-modifying effects in JAKi naïve MF patients.

Figure 16:
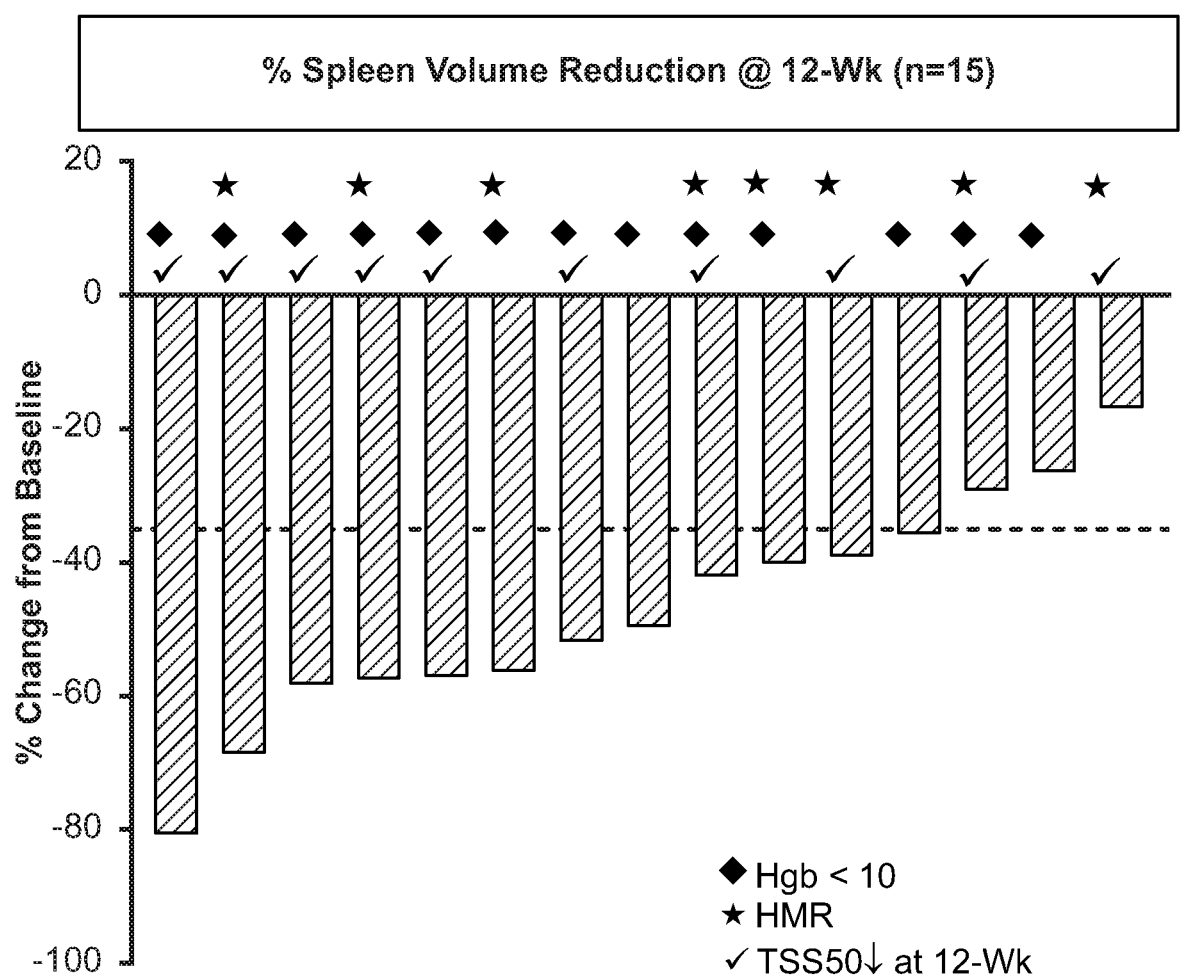
FIG. 16 illustrates the percent spleen reduction volume at 12 weeks after treatment with Compound 1 in JAK inhibitor naïve (Arm 3) patients with myelofibrosis.
Figure 17:
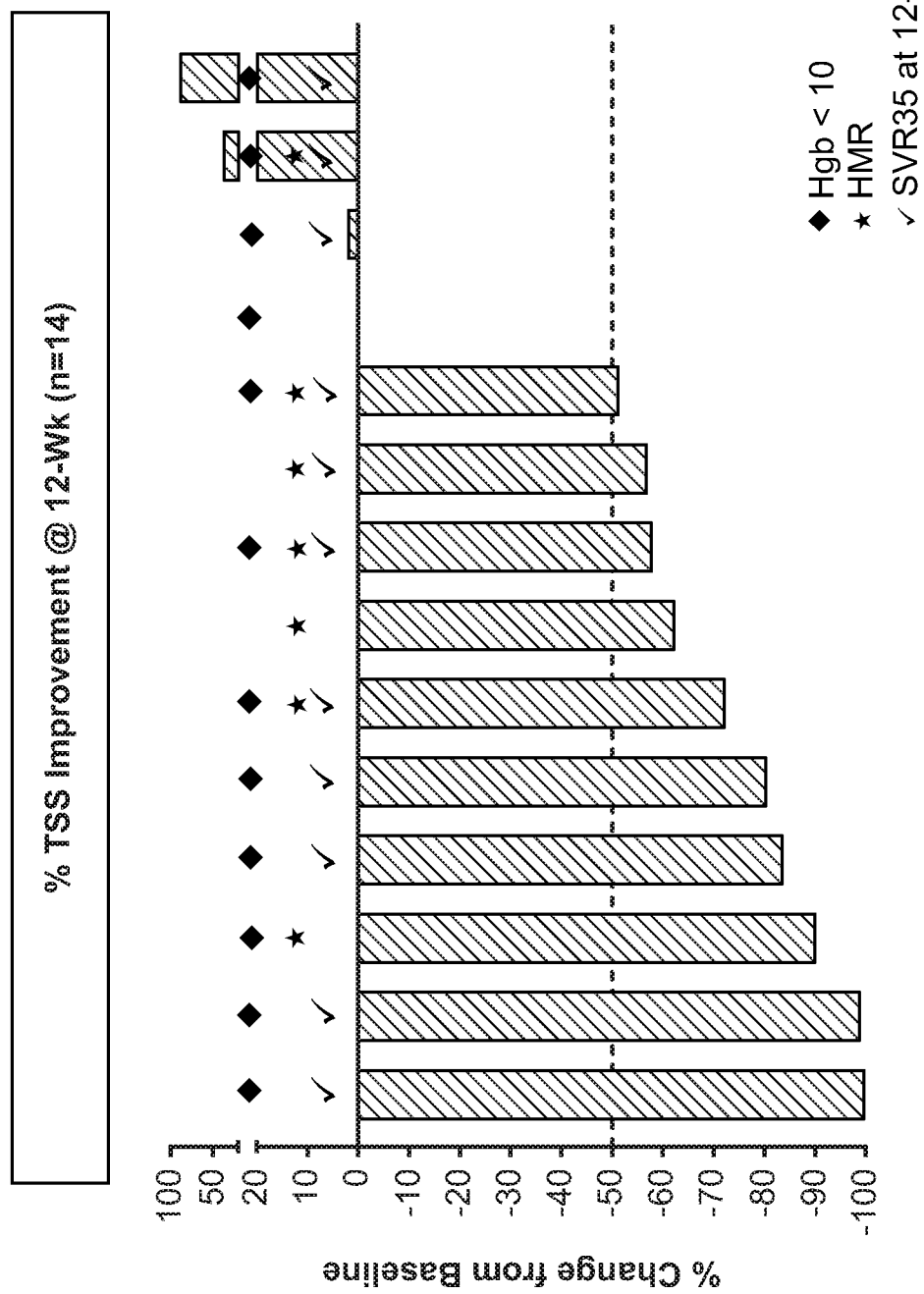
FIG. 17 illustrates the percent total symptom score improvement after treatment with Compound 1 in JAK inhibitor naïve (Arm 3) patients with myelofibrosis.
Figure 18:
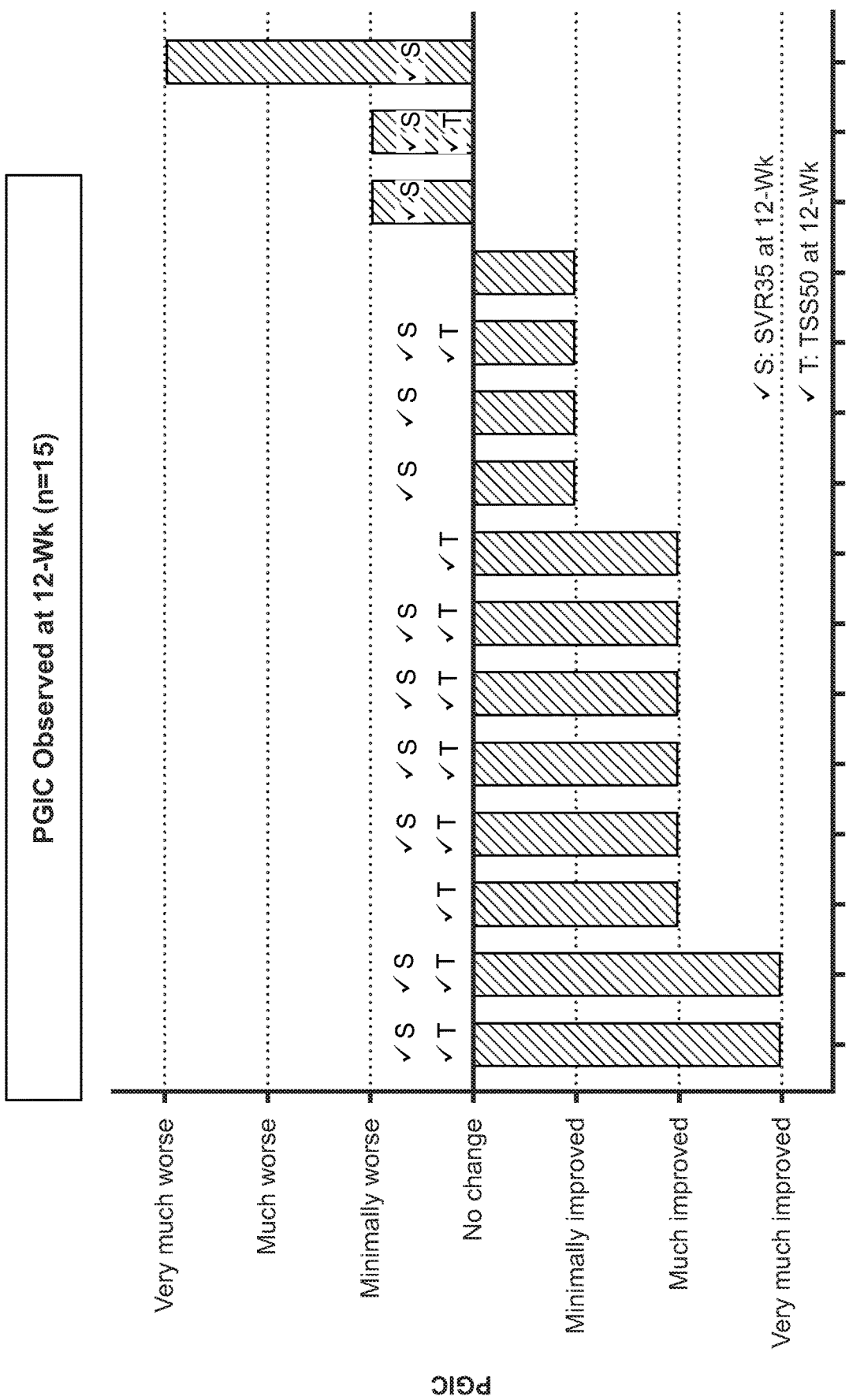
FIG. 18 illustrates the Patient Global Impression of Change after treatment with Compound 1 in JAK inhibitor naïve (Arm 3) patients with myelofibrosis.

An expanded patient population (n=15) for Arm 3 were treated for at least 12 weeks. About 80% of patients achieved ≥35% SVR with an average of about −49.7%. See FIG. 16. Hgb was less than 10 g/dL and DIPSS score was int-2 or higher. In addition, about 71% of patients had a TSS of ≥10 (see FIG. 17) and about 80% of patients had an overall improvement in PGIC (see FIG. 18).

Time Point 2

Patients were added to the study following the first data cut and treatment was continued for approximately 25.9 weeks (median, range: 0.4, 116.6). A summary of the results from the trial are provided below.

Figure 10A:
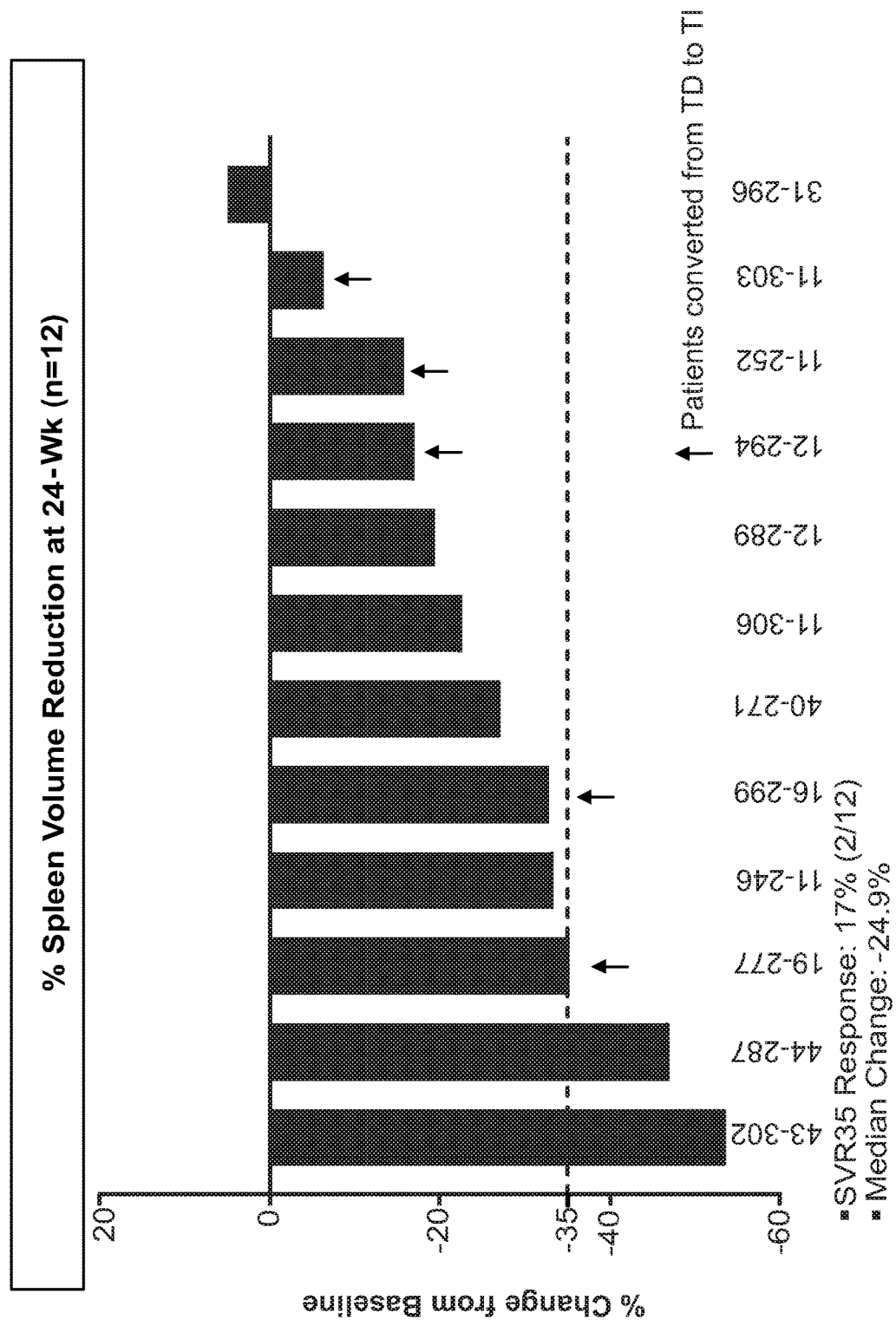
FIG. 10A illustrates the percent spleen reduction volume at 24 weeks after treatment with Compound 1 as an add-on to ruxolitinib (Arm 2) in patients with refractory or intolerant myelofibrosis subjects who were transfusion dependent at the start of therapy.
Figure 10B:
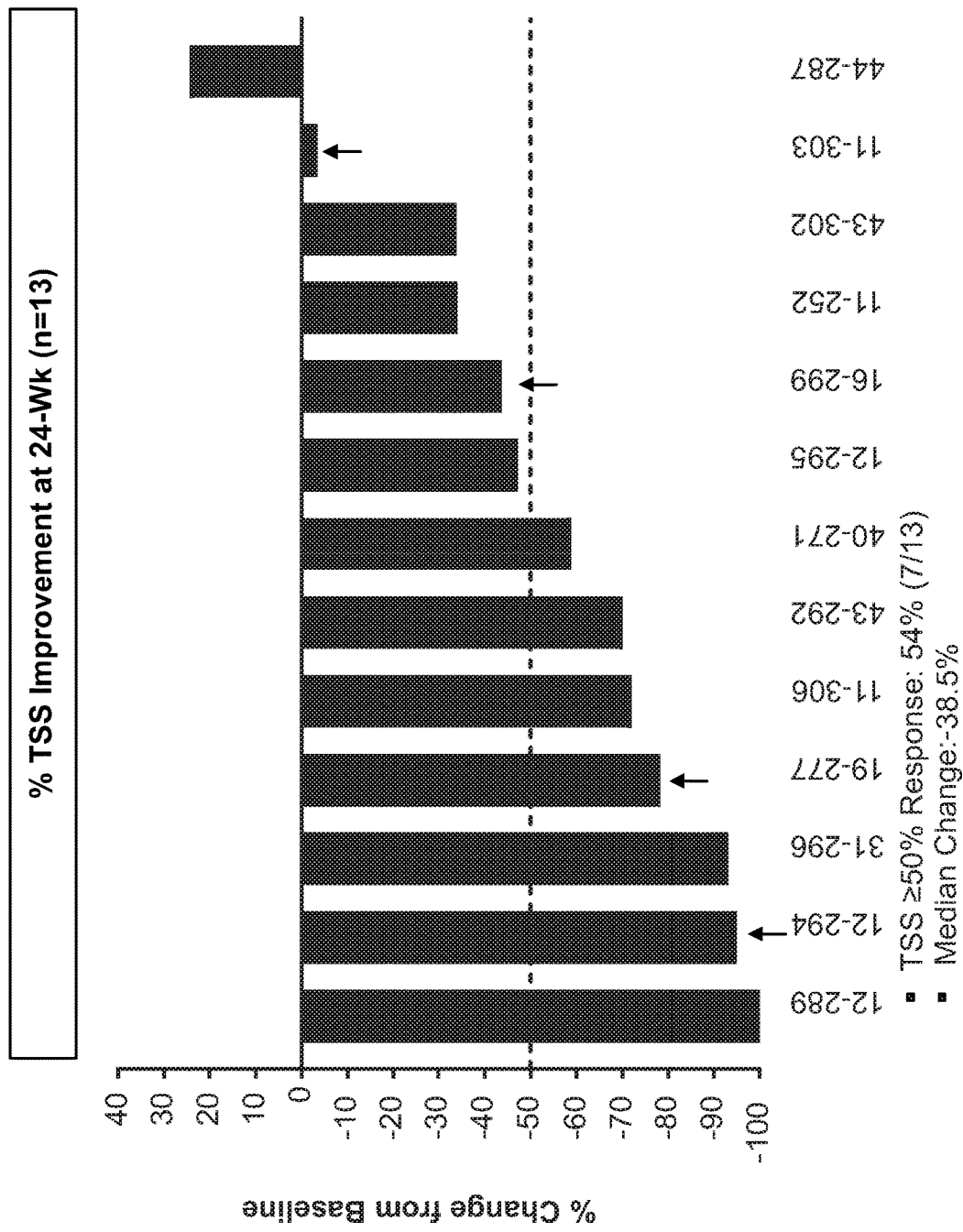
FIG. 10B illustrates the percent total symptom score improvement after treatment with Compound 1 as an add-on to ruxolitinib (Arm 2) in patients with refractory or intolerant myelofibrosis subjects who were transfusion dependent at the start of therapy.
Figure 10C:
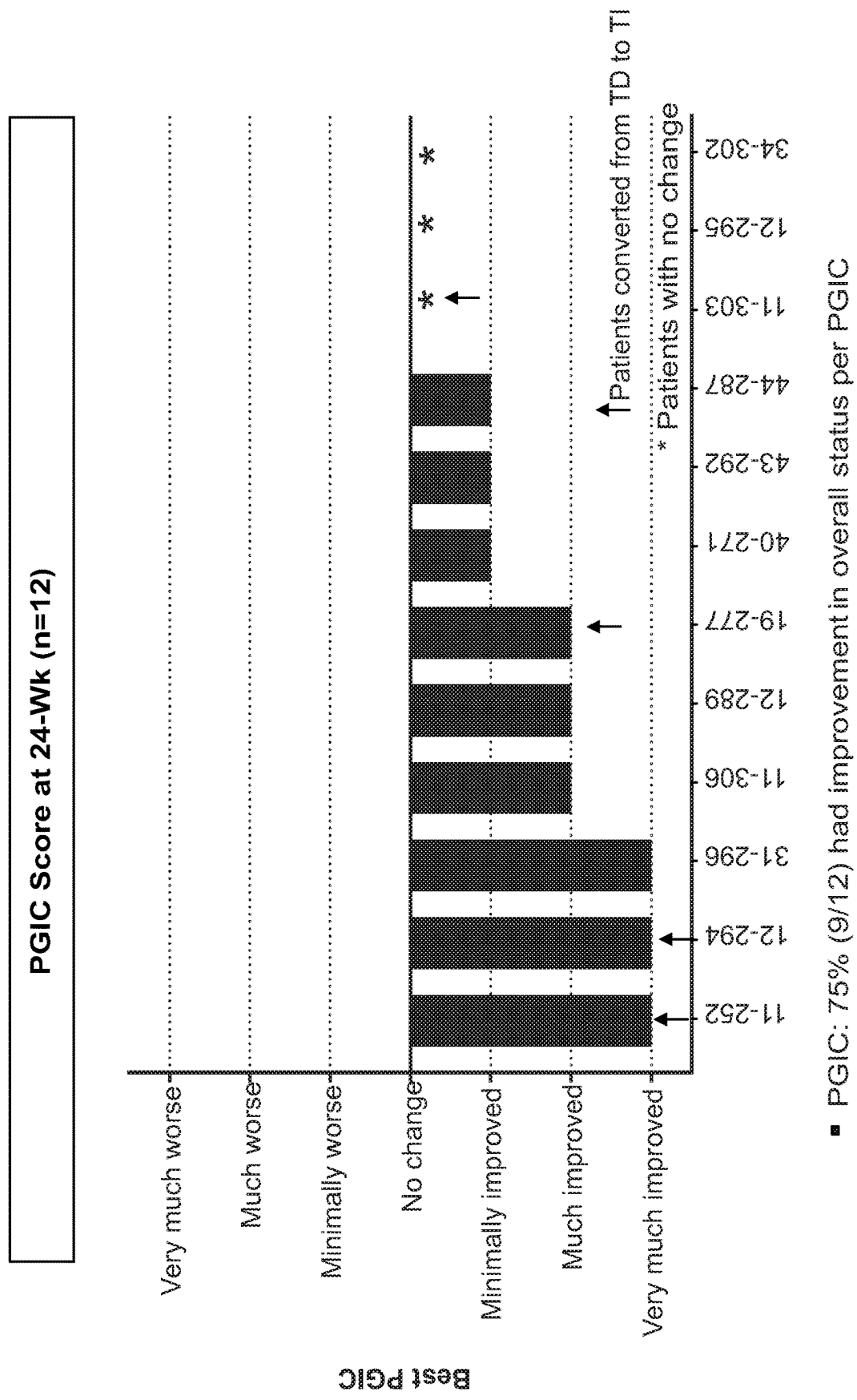
FIG. 10C illustrates the Patient Global Impression of Change after treatment with Compound 1 as an add-on to ruxolitinib (Arm 2) in patients with refractory or intolerant myelofibrosis subjects who were transfusion dependent at the start of therapy.
Figure 11A:
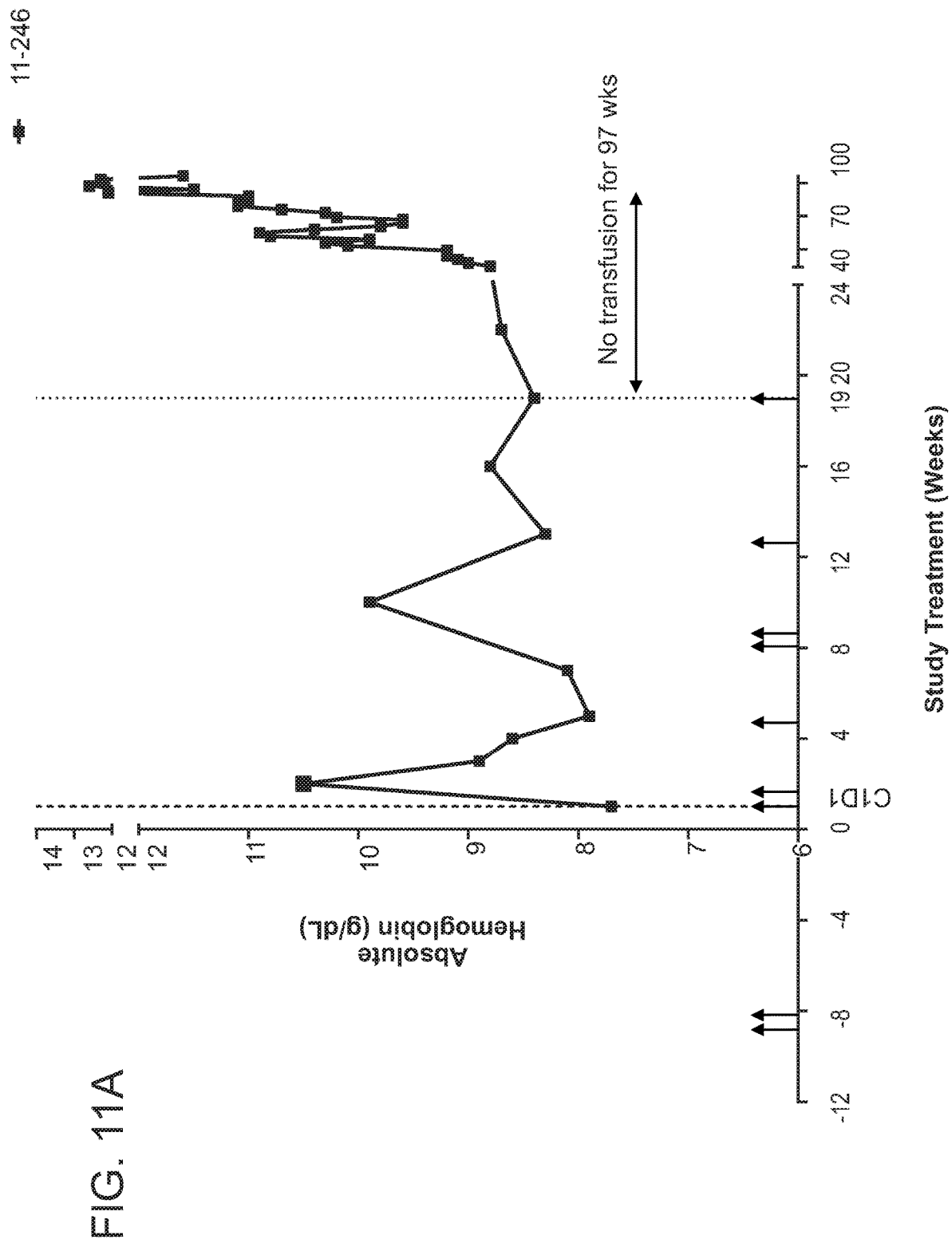
FIG. 11A illustrates the absolute hemoglobin and transfusion requirement for patient 11-246 following treatment with Compound 1 as an add-on to ruxolitinib (Arm 2).
Figure 11B:
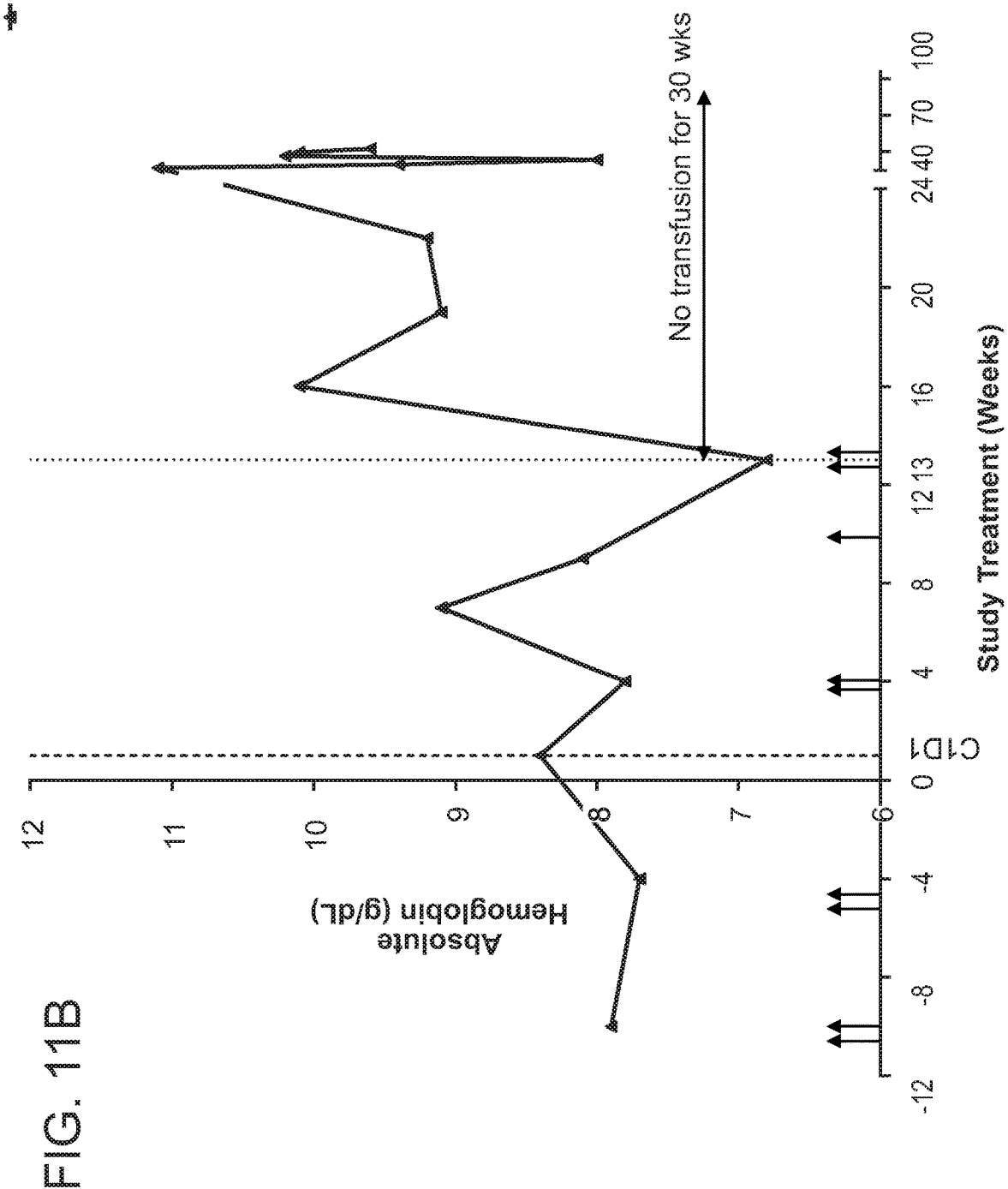
FIG. 11B illustrates the absolute hemoglobin and transfusion requirement for patient 19-277 following treatment with Compound 1 as an add-on to ruxolitinib (Arm 2).
Figure 11C:
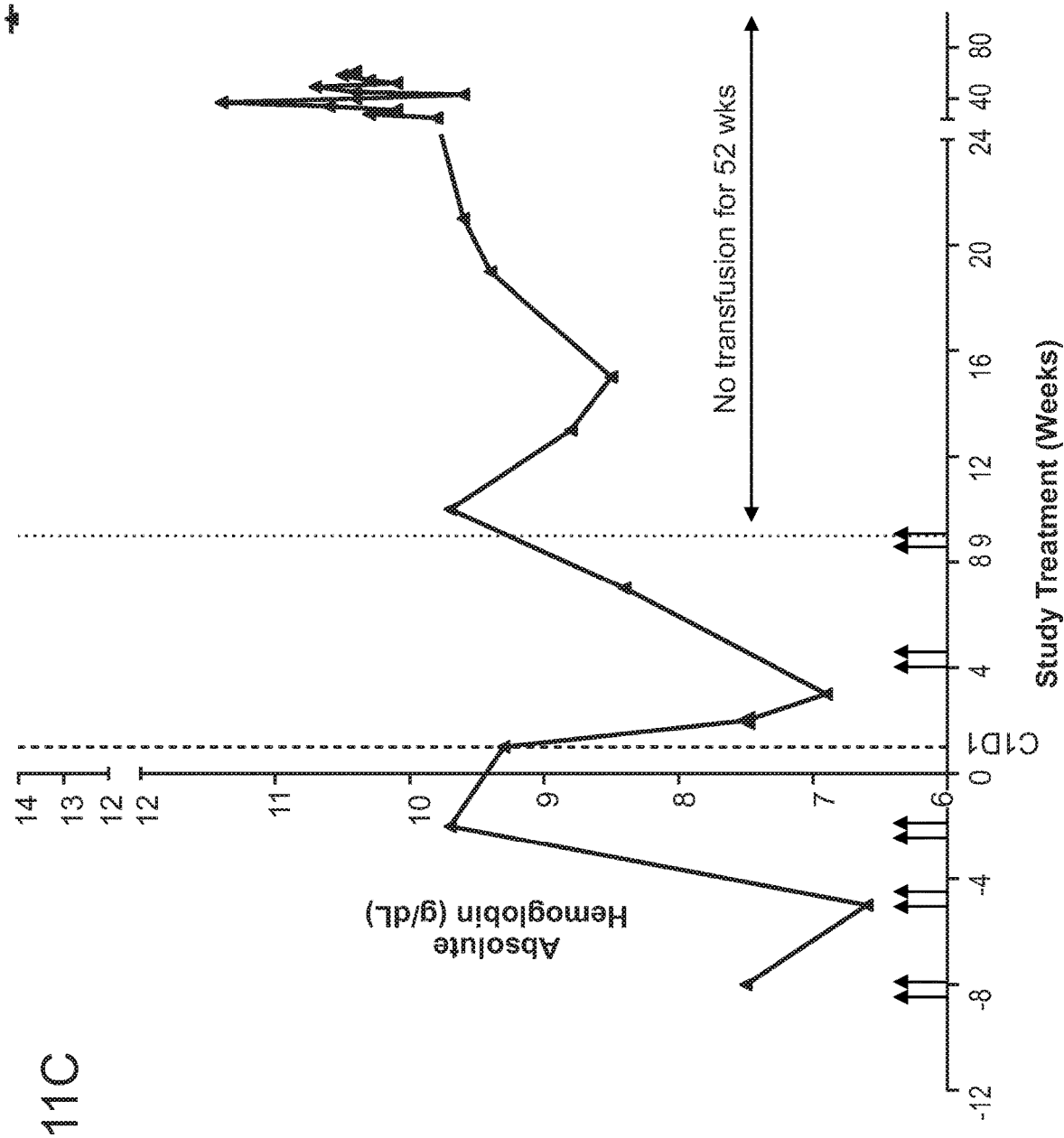
FIG. 11C illustrates the absolute hemoglobin and transfusion requirement for patient 11-252 following treatment with Compound 1 as an add-on to ruxolitinib (Arm 2).
Figure 11D:
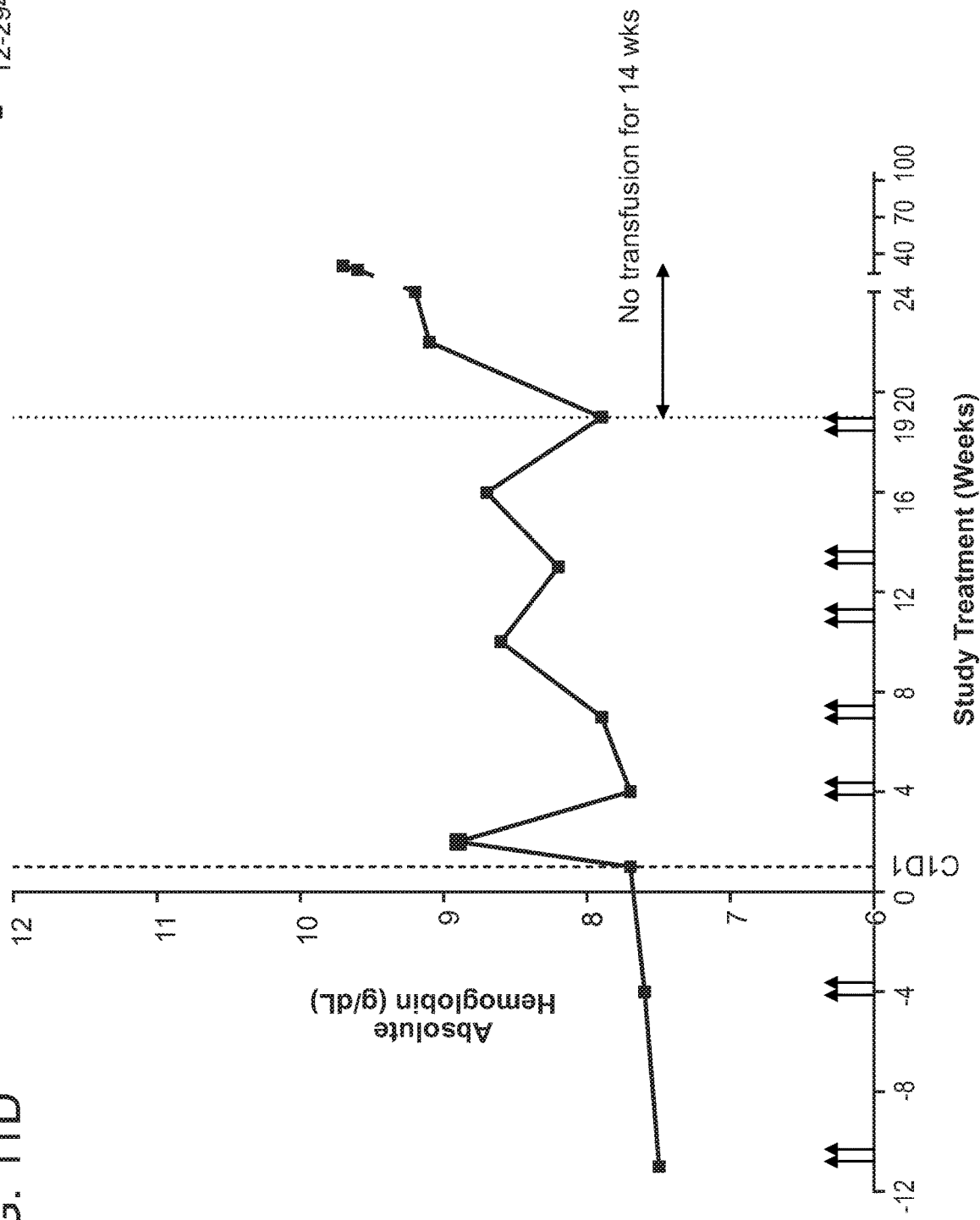
FIG. 11D illustrates the absolute hemoglobin and transfusion requirement for patient 12-294 following treatment with Compound 1 as an add-on to ruxolitinib (Arm 2).

FIGS. 10A-C illustrates the 24 week results from treatment with Compound 1 as an add-on to ruxolitinib (Arm 2) in patient's with refractory or intolerant myelofibrosis subjects who were transfusion dependent at the start of therapy. At 24 weeks, about 35% of patients converted from transfusion dependent to transfusion independent as represented by the upward arrows (FIG. 10A). The average spleen volume reduction was about −24.9%. About 76.5% of patients had improvement in disease symptoms per total symptom score (TSS) about 75% of patients had improved Patient Global Impression of Change (PGIC). See FIGS. 10B and 10C. Further, about 63% of patients showed improvement in bone marrow fibrosis (data not shown).

FIGS. 11A-D shows the absolute hemoglobin values and transfusion requirements for representative patients from Arm 2. The average time of conversion from transfusion dependent (TD) to transfusion independent (TI) was about 14 weeks. The average transfusion free time post-conversion was about 14 weeks with a maximum of 85 weeks. About 41% of patients had greater than or equal to a 50% reduction in transfusion intensity.

Figure 12A:
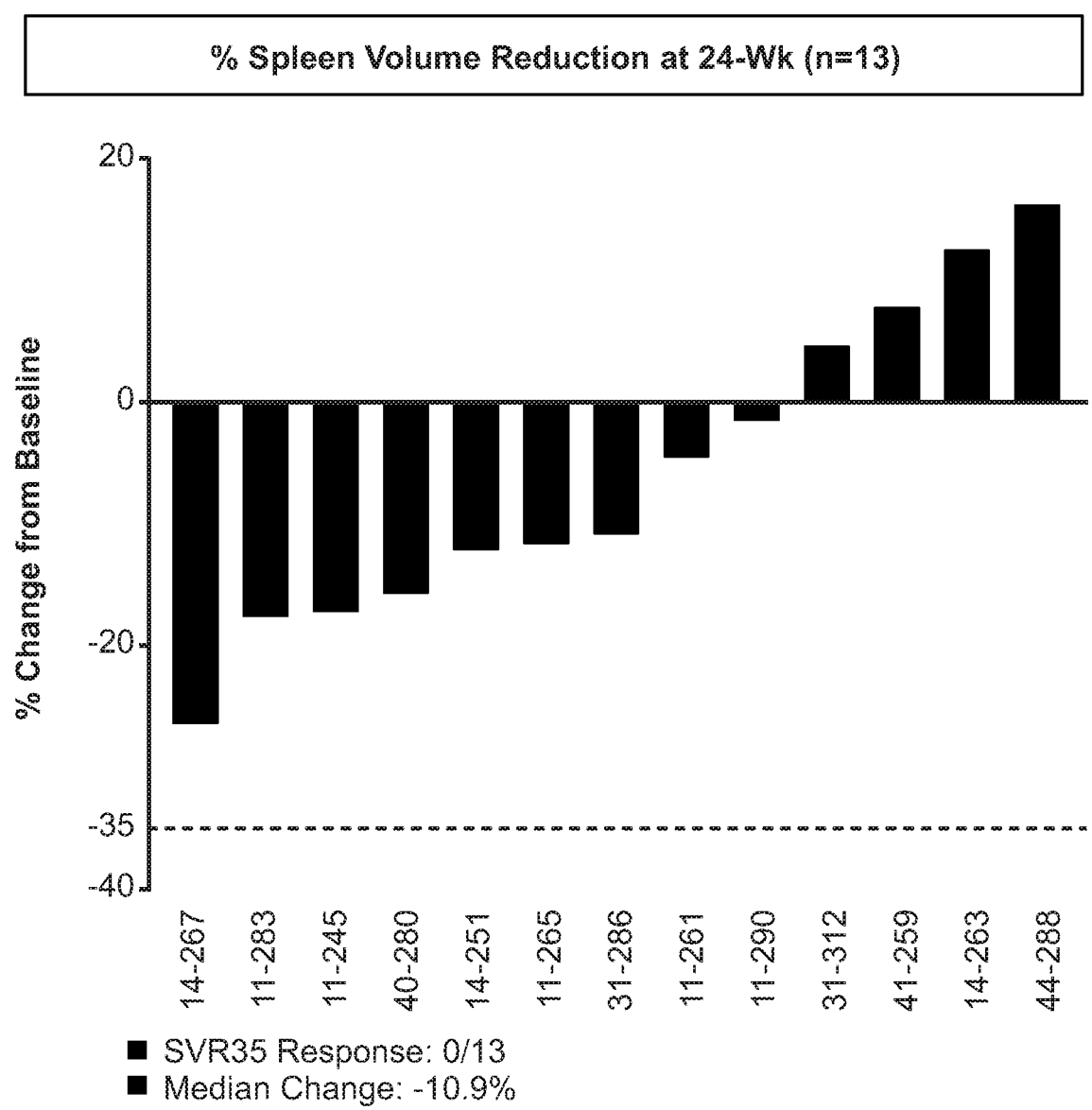
FIG. 12A illustrates the percent spleen reduction volume at 24 weeks after treatment with Compound 1 as an add-on to ruxolitinib (Arm 2) in patients with refractory or intolerant myelofibrosis who were non-transfusion dependent at the start of therapy.
Figure 12B:
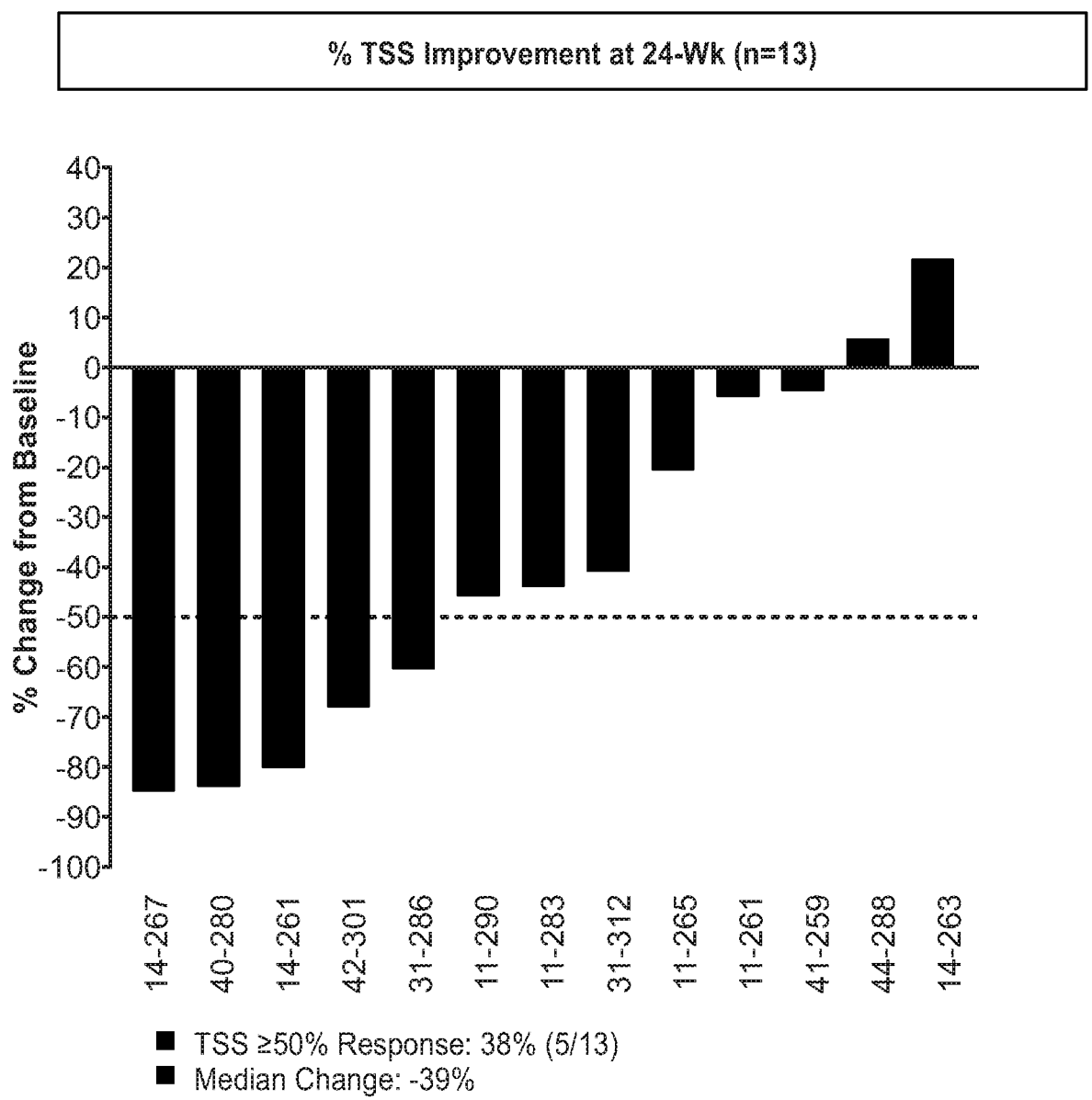
FIG. 12B illustrates the percent total symptom score improvement after treatment with Compound 1 as an add-on to ruxolitinib (Arm 2) in patients with refractory or intolerant myelofibrosis who were non-transfusion dependent at the start of therapy.
Figure 12C:
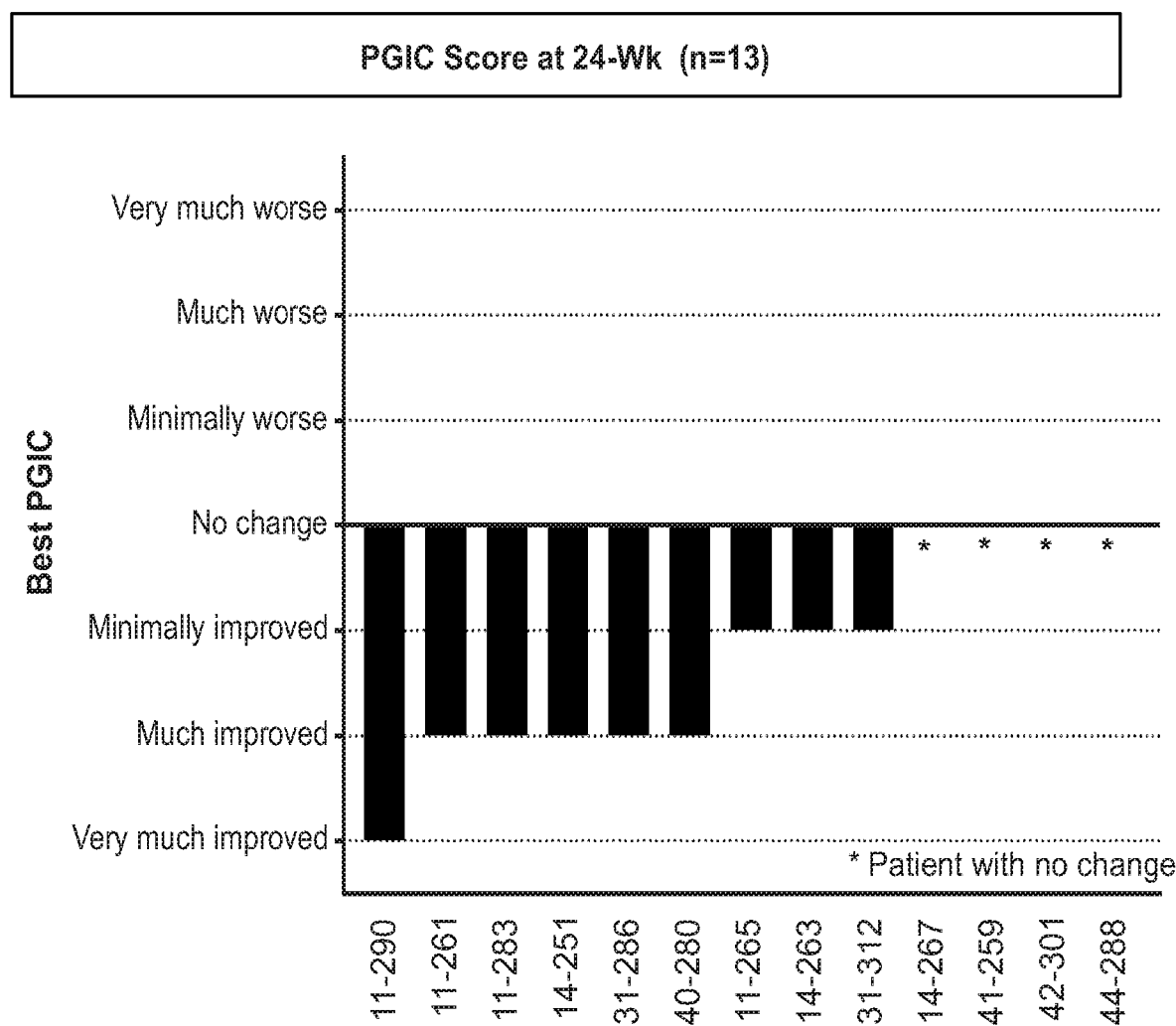
FIG. 12C illustrates the Patient Global Impression of Change after treatment with Compound 1 as an add-on to ruxolitinib (Arm 2) in patients with refractory or intolerant myelofibrosis who were non-transfusion dependent at the start of therapy.

FIGS. 12A-C illustrates the 24 week results from treatment with Compound 1 as an add-on to ruxolitinib (Arm 2) in patients with refractory or intolerant myelofibrosis subjects who were non-transfusion dependent at the start of therapy. At 24 weeks, the average spleen volume reduction was about −10.9% (FIG. 12A). About 38% of patients had improvement in disease symptoms per total symptom score (TSS) about 69% of patients had improved Patient Global Impression of Change (PGIC). See FIGS. 12B and 12C.

Further, about 25% of patients showed improvement in bone marrow fibrosis (data not shown).

Figure 13A:
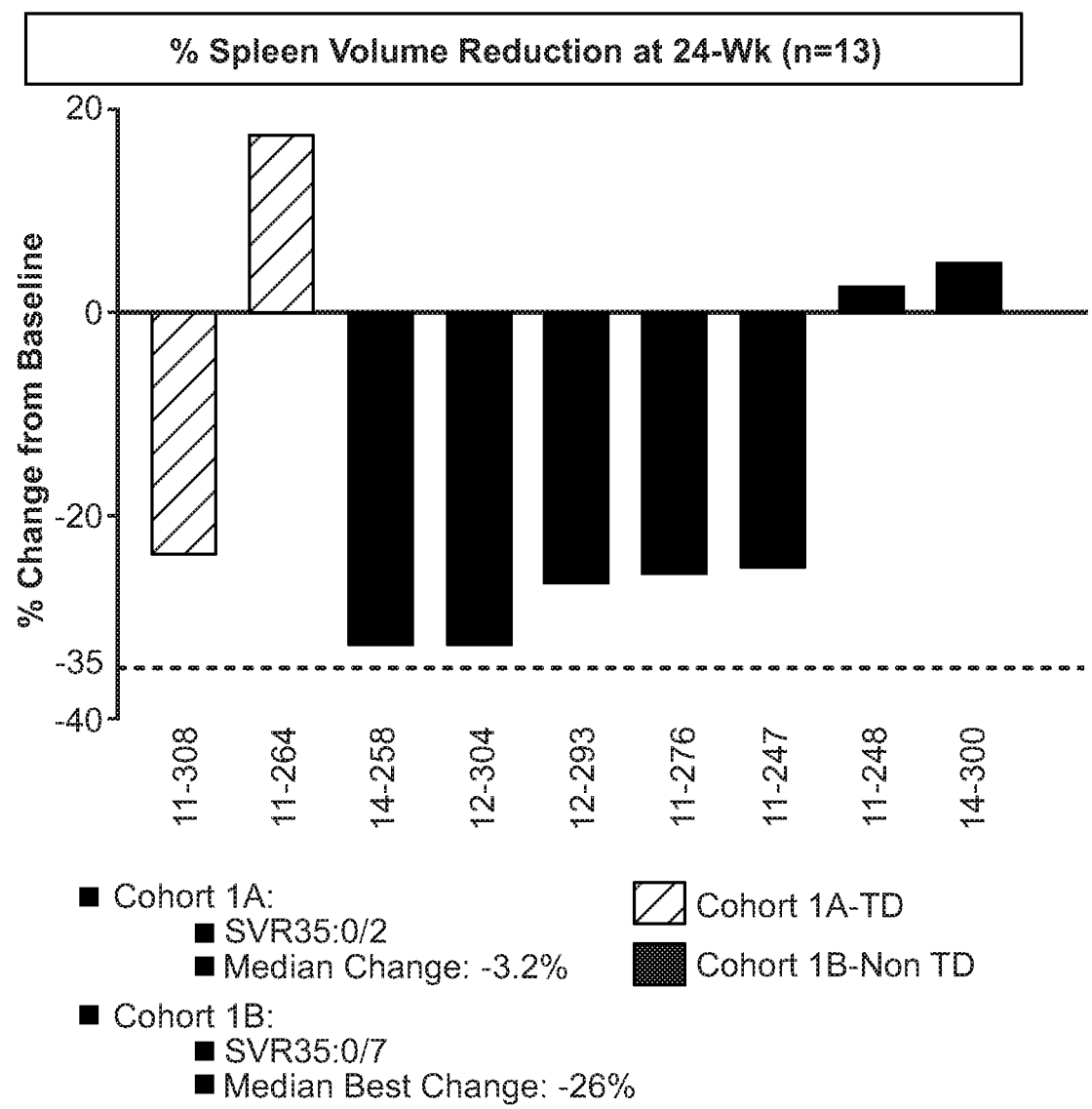
FIG. 13A illustrates the percent spleen reduction volume at 24 weeks after treatment with Compound 1 monotherapy (Arm 1) in patients with refractory or intolerant myelofibrosis who were transfusion (Cohort 1A) or non-transfusion dependent (Cohort 1B) at the start of therapy.
Figure 15A:
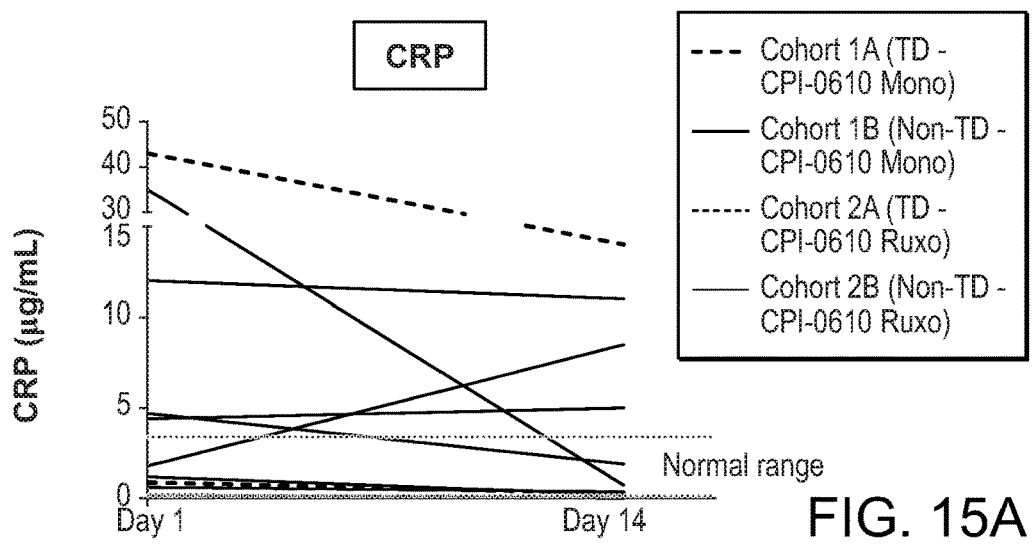
FIG. 15A illustrates the reduction of CRP in patients with refractory or intolerant myelofibrosis who were transfusion or non-transfusion dependent at the start of therapy and were treated with Compound 1 alone, i.e., monotherapy.
Figure 15B:
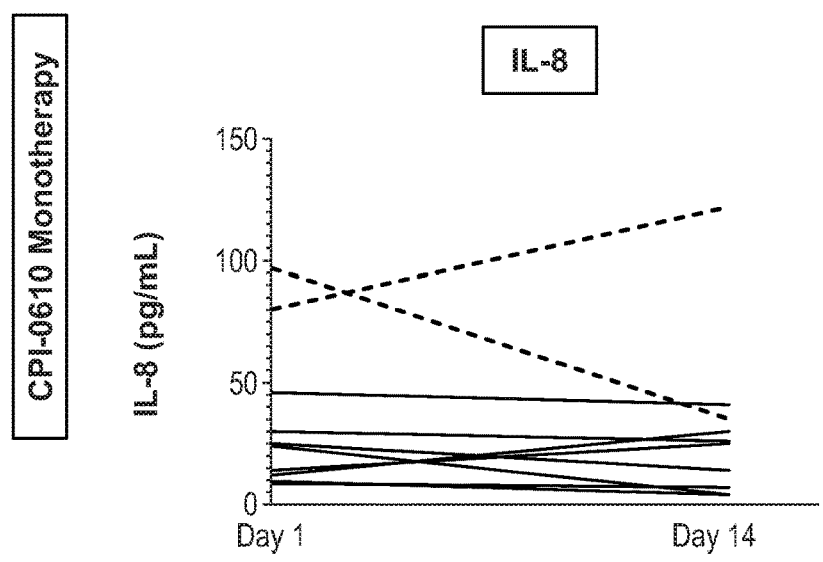
FIG. 15B illustrates the reduction of IL-8 in patients with refractory or intolerant myelofibrosis who were transfusion or non-transfusion dependent at the start of therapy and were treated with Compound 1 alone, i.e., monotherapy.
Figure 15C:
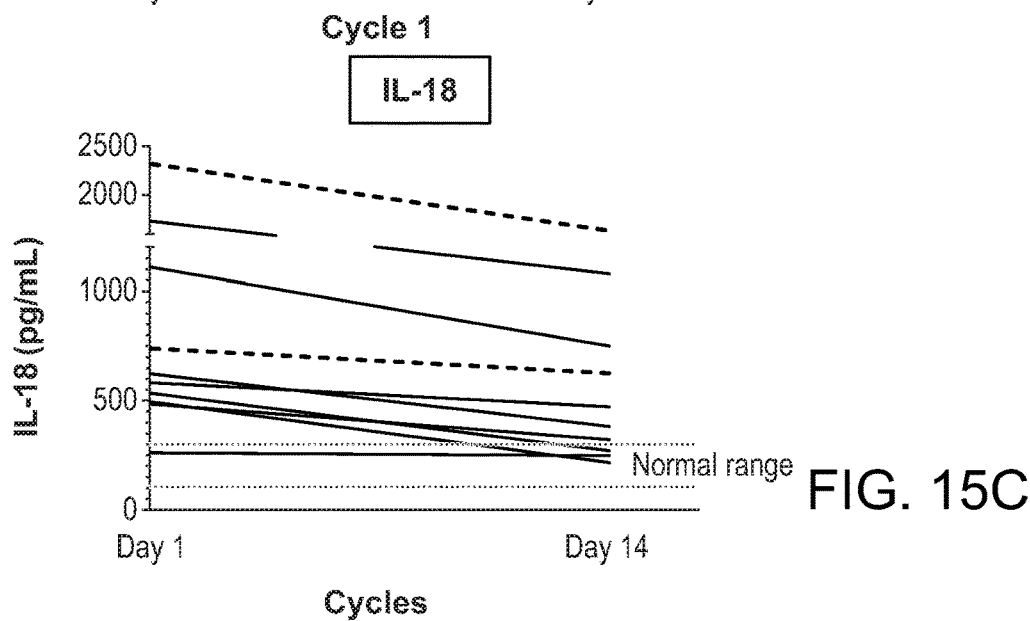
FIG. 15C illustrates the reduction of IL-18 in patients with refractory or intolerant myelofibrosis who were transfusion or non-transfusion dependent at the start of therapy and were treated with Compound 1 alone, i.e., monotherapy.
Figure 15D:
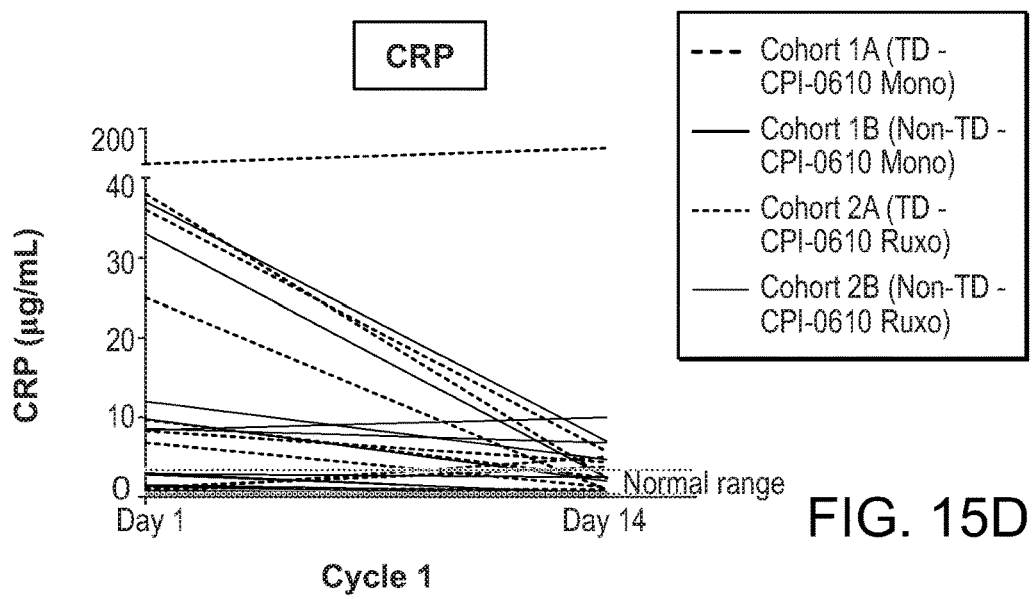
FIG. 15D illustrates the reduction of CRP in patients with refractory or intolerant myelofibrosis who were transfusion or non-transfusion dependent at the start of therapy and were treated with Compound 1 as an add-on to ruxolitinib.
Figure 15E:
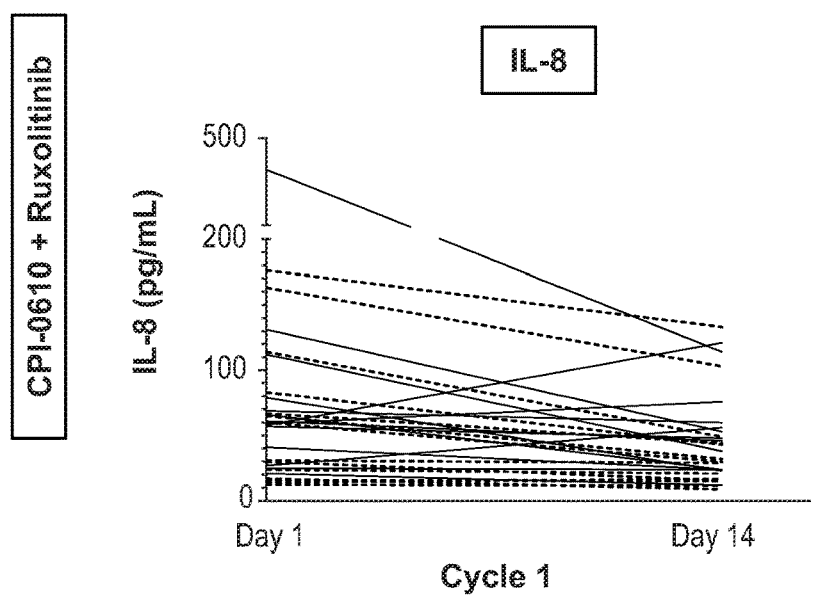
FIG. 15E illustrates the reduction of IL-8 in patients with refractory or intolerant myelofibrosis who were transfusion or non-transfusion dependent at the start of therapy and were treated with Compound 1 as an add-on to ruxolitinib.
Figure 15F:
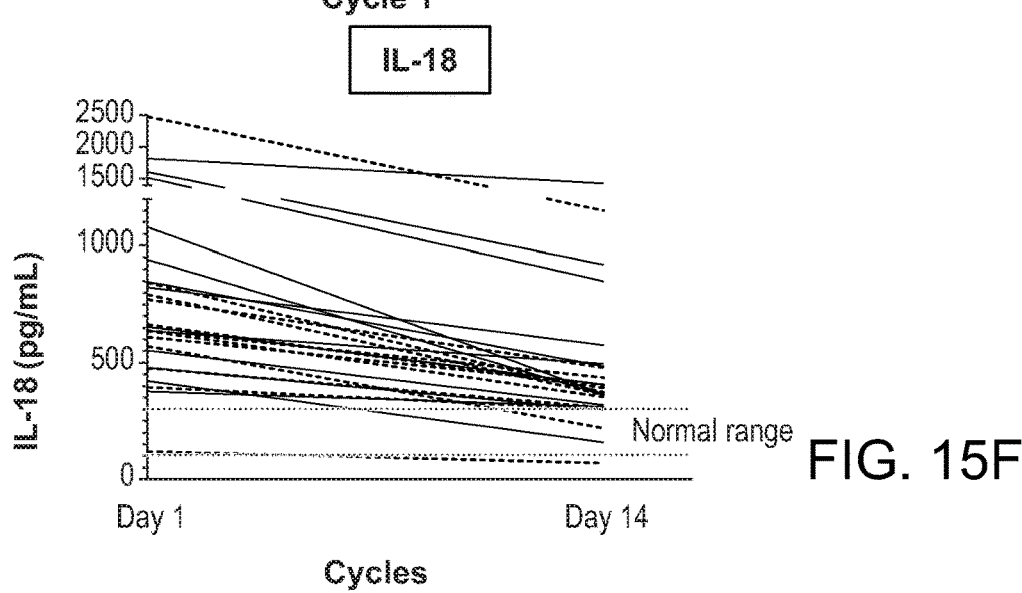
FIG. 15F illustrates the reduction of IL-18 in patients with refractory or intolerant myelofibrosis who were transfusion or non-transfusion dependent at the start of therapy and were treated with Compound 1 as an add-on to ruxolitinib.

FIGS. 13A-C illustrates the 24 week results from treatment with Compound 1 monotherapy (Arm 1) in patients with refractory or intolerant myelofibrosis subjects who were transfusion (Cohort 1A) or non-transfusion dependent (Cohort 1B) at the start of therapy. At 24 weeks, the average spleen volume reduction was about −3.2% for TD patients and about −26% for non-TD patients (FIG. 13A). About 60% of non-TD patients had improvement in disease symptoms per total symptom score (TSS) about 50% of TD and 100% of non-TD patients had improved Patient Global Impression of Change (PGIC). See FIGS. 13B and 13C. Further, about 25% of TD patients showed improvement in bone marrow fibrosis (data not shown).

The improvement in bone marrow fibrosis from Arms 1 and 2 were also evaluated. See FIG. 14. It was found that about 38% of subjects had bone marrow fibrosis improvement with about 32% having improvement as early as 6-months. Additionally, the best improvement in bone marrow fibrosis was seen in Cohort 2B (See FIG. 7) at 63% of patients having improvement, i.e., those patients who were transfusion dependent at the start of therapy and were given Compound 1 as an add-on to ruxolitinib.

Pro-inflammatory cytokine levels showed a trend toward normalization within 14 days for both monotherapy and combination therapy arms. See FIGS. 15A-F.

While have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of treating myelofibrosis in a subject comprising administering to the subject a therapeutically effective amount of 2-((4S)-6-(4-chlorophenyl)-1-methyl-4H-benzo[c]isoxazolo[4,5-e]azepin-4-yl)acetamide, or a pharmaceutically acceptable salt thereof.

2. The method of claim 1, wherein the subject has previously undergone treatment with a janus kinase (JAK) inhibitor.

3. The method of claim 1, wherein the subject is progressed/relapsed to a JAK inhibitor.

4. The method of claim 1, wherein the subject is refractory/resistant to a JAK inhibitor.

5. The method of claim 1, wherein the subject is intolerant to a JAK inhibitor.

6. The method of claim 1, wherein the subject has previously undergone treatment with ruxolitinib.

7. The method of claim 1, wherein the subject is a janus kinase (JAK) inhibitor naïve subject.

8. The method of claim 1, further comprising administering to the subject a therapeutically effective amount of a janus kinase (JAK) inhibitor.

9. The method of claim 8, wherein the subject is a janus kinase (JAK) inhibitor naïve subject prior to treatment.

10. The method of claim 8, wherein the JAK inhibitor is ruxolitinib.

11. The method of claim 1, wherein the subject is cytopenic.

12. The method of claim 1, wherein the subject is anemic.

13. The method of claim 1, wherein the subject has a hemoglobin count of less than 10 g/dL.

14. The method of claim 1, wherein the subject is thrombocytopenic.

15. The method of claim 1, wherein the subject's platelet count is less than 120,000 platelets/µL.

16. The method of claim 1, wherein the subject is thrombocytemic.

17. The method of claim 1, wherein the subject's platelet count is more than 400,000 platelets/µL.

18. The method of claim 1, wherein the subject's platelet count is more than 500,000 platelets/µL.

19. The method of claim 1, wherein the subject is neutropenic.

20. The method of claim 1, wherein the subject's absolute neutrophil count is less than 1000 neutrophils/µL of blood.

21. The method of claim 1, wherein the subject has an enlarged spleen or liver.

22. The method of claim 1, wherein the subject is suffering from abdominal discomfort, dyspnea on exertion, early satiety, fatigue, headaches, night sweats, dizziness, insomnia, pruritus, or bone pain.

23. The method of claim 1, wherein the subject is transfusion dependent.

24. The method of claim 1, wherein the subject is administered from 100 mg/day to 300 mg/day of 2-((4S)-6-(4-chlorophenyl)-1-methyl-4H-benzo [c]isoxazolo[4,5-e]azepin-4-yl)acetamide.

25. The method of claim 1, wherein the subject is administered 2-((4S)-6-(4-chlorophenyl)-1-methyl-4H-benzo[c]isoxazolo[4,5-e]azepin-4-yl)acetamide once per day.

26. The method of claim 1, wherein the subject is administered a pharmaceutically acceptable salt of 6-(4-chlorophenyl)-1-methyl-4H-benzo[c]isoxazolo[4,5-e]azepin-4-yl)acetamide.

27. The method of claim 1, wherein the subject is administered 2-((4S)-6-(4-chlorophenyl)-1-methyl-4H-benzo[c]isoxazolo[4,5-e]azepin-4-yl)acetamide.

28. The method of claim 1, wherein the subject's platelet count is more than 450,000 platelets/µL.

29. The method of claim 1, wherein the subject's platelet count is more than 600,000 platelets/µL.

30. The method of claim 1, wherein the subject is administered from 50 mg/day to 500 mg/day 2-((4S)-6-(4-chlorophenyl)-1-methyl-4H-benzo[c]isoxazolo[4,5-e]azepin-4-yl) acetamide or a pharmaceutically acceptable salt thereof.

* * * * *